US010492511B2

(12) United States Patent
Kulke et al.

(10) Patent No.: US 10,492,511 B2
(45) Date of Patent: Dec. 3, 2019

(54) PREPARATIONS

(71) Applicant: Symrise AG, Holzminden (DE)

(72) Inventors: Torsten Kulke, Höxter-Luchtringen (DE); Sven Siegel, Höxter (DE); Michael Backes, Holzminden (DE); Benoit Join, Holzminden (DE); Hubert Loges, Höxter (DE); Günter Kindel, Höxter (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 15/799,180

(22) Filed: Oct. 31, 2017

(65) Prior Publication Data

US 2018/0049449 A1 Feb. 22, 2018

Related U.S. Application Data

(62) Division of application No. 14/651,490, filed as application No. PCT/EP2012/075198 on Dec. 12, 2012, now Pat. No. 10,182,584.

(51) Int. Cl.
A23G 4/06 (2006.01)
A61Q 19/10 (2006.01)
A61Q 17/04 (2006.01)
A61Q 11/00 (2006.01)
A61Q 5/00 (2006.01)
A61Q 19/00 (2006.01)
A61K 31/497 (2006.01)
A61K 31/4436 (2006.01)
A61K 31/426 (2006.01)
A61K 31/42 (2006.01)
A61K 31/4155 (2006.01)
A61K 31/381 (2006.01)
A61K 31/357 (2006.01)
A61K 31/343 (2006.01)
A61K 31/216 (2006.01)
A61K 31/045 (2006.01)
A61K 8/69 (2006.01)
A61K 8/49 (2006.01)
A61K 8/42 (2006.01)
A61K 8/37 (2006.01)
A61K 8/34 (2006.01)
A61K 8/02 (2006.01)
A23L 29/00 (2016.01)
A23L 27/20 (2016.01)

(52) U.S. Cl.
CPC ............ A23G 4/06 (2013.01); A23L 27/204 (2016.08); A23L 29/045 (2016.08); A61K 8/02 (2013.01); A61K 8/34 (2013.01); A61K 8/37 (2013.01); A61K 8/42 (2013.01); A61K 8/4986 (2013.01); A61K 8/69 (2013.01); A61K 31/045 (2013.01); A61K 31/216 (2013.01); A61K 31/343 (2013.01); A61K 31/357 (2013.01); A61K 31/381 (2013.01); A61K 31/4155 (2013.01); A61K 31/42 (2013.01); A61K 31/426 (2013.01); A61K 31/4436 (2013.01); A61K 31/497 (2013.01); A61Q 5/00 (2013.01); A61Q 11/00 (2013.01); A61Q 17/04 (2013.01); A61Q 19/00 (2013.01); A61Q 19/10 (2013.01); A61K 2300/00 (2013.01); A61K 2800/244 (2013.01)

(58) Field of Classification Search
None
See application file for complete search history.

(56) References Cited

U.S. PATENT DOCUMENTS

| | | | |
|---|---|---|---|
| 4,157,384 A | 6/1979 | Watson et al. | |
| 5,843,466 A | 12/1998 | Mane et al. | |
| 6,328,982 B1 | 12/2001 | Shiroyama et al. | |
| 6,503,517 B1* | 1/2003 | Mohammadi | A61K 8/0212 424/401 |
| 2003/0072842 A1 | 4/2003 | Johnson et al. | |
| 2006/0210482 A1 | 9/2006 | Cassara | |
| 2008/0089850 A1* | 4/2008 | Haskel | A61K 8/34 424/49 |
| 2009/0054520 A1* | 2/2009 | Surburg | A23G 3/36 514/529 |

FOREIGN PATENT DOCUMENTS

| | | | | |
|---|---|---|---|---|
| EP | 1332772 A2 | 8/2003 | | |
| WO | 03043431 A1 | 5/2003 | | |
| WO | 2012061698 A2 | 5/2012 | | |
| WO | WO-2012061698 A2 * | 5/2012 | ........... | C07C 233/11 |

OTHER PUBLICATIONS

Leffingwell, JC. Burnt Sugar, Caramel & Maple Notes, copyright 2010. Downloaded Jan. 3, 2019 fromhttp://www.leffingwell.com/burnt.htm). (Year: 2010).*
Karashima et al., "Bimodal Action of Menthold on the Transient Receptor Potential Channel TRPA1", The Journal of Neuroscience (Sep. 12, 2007), 27(37): 9874-9884.
Sajilata et al., "Tea Polyphenols as Nutraceuticals", Institute of Food Technologies (2008) 7: 229-254.

* cited by examiner

Primary Examiner — Michael P Cohen
(74) Attorney, Agent, or Firm — Dilworth & Barrese, LLP

(57) ABSTRACT

Proposed are preparations, comprising special amides and menthol or menthol compounds or aromatic substances, characterized in that they have improved flavor and scent properties, and also that they allow the production of preparations, particularly emulsions with improved shelf life.

20 Claims, No Drawings

PREPARATIONS

CROSS REFERENCE TO RELATED APPLICATIONS

The present application is a divisional application of co-pending U.S. application Ser. No. 14/651,490 filed Jun. 11, 2015, the entire contents of which are incorporated by reference herein.

FIELD OF THE INVENTION

The invention pertains to the areas of cosmetics, pharmacy, and food products and concerns preparations having a cooling effect on the skin or mucosa that contain menthol or menthol compounds or aromatic substances together with selected amides.

PRIOR ART

Although menthol has already been known as a cooling substance for many decades and is still indispensable today in numerous applications, this substance has a long series of drawbacks: it is volatile, has a strong odor, and has a bitter taste. At higher concentrations, it no longer provides a pleasant cooling sensation, but stings or burns. Finally, menthol cannot be formulated as desired, as it can interact with other chemical components. This has led to the development of a wide variety of menthol compounds, a number of which show improved flavor properties.

International Patent Application WO 2012 061698 A2 (Senomyx) discloses complex amides that can be used as TRPM8 modulators (Transient Receptor Potential Channel Melastin Member 8). This refers to substances that are capable of producing hot or cold sensations on the skin or mucosa. These substances are particularly recommended for use in food and body care products.

Despite the progress made in recent years and the development of increasingly effective cooling agents having a terpene structure, there is still a need, both in cosmetics and in the area of food products, for cooling agents or synergistic cooling agent mixtures that show improved sensory properties, can be more easily formulated, have a beneficial effect on the end product from the standpoint of applications engineering, and in particular, have an effect on the skin or mucosa that can be subjectively perceived as equally strong despite low application concentrations.

The object of the present invention is therefore to provide preparations of the type described above.

DESCRIPTION OF THE INVENTION

A first object of the invention concerns preparations having a cooling effect, containing
(a) amides of formula (I)

$$A^1\text{-}[B]\text{-}CO\text{—}NR^a\text{—}(CH_2)_p A^2 \qquad (I)$$

wherein
$A^1$ denotes an optionally substituted aryl, heteroaryl, or cycloalkyl residue,
B denotes an $OCR^b R^b$, $CHR^c\text{—}CHR^d$, $CR^e\text{=}CR^f$, or cycloalkyl residue,
p denotes numbers from 1 to 3,
$R^a$ denotes an optionally substituted alkyl, heteroalkyl, alkenyl, heteroalkenyl, aryl, aralkyl, heteroarylcyclo or heterocycloalkyl residue with 1 to 20 carbon atoms,
$R^b$, $R^c$, $R^d$, $R^e$ and $R^f$ independently denote hydrogen or an alkyl residue with 1 to 4 carbon atoms, and
$A^2$ denotes an optionally substituted five- or six-membered heteroaryl residue that has at least one heteroatom from the group composed of nitrogen, oxygen and sulfur,
as well as salts thereof, and
(b1) menthol and/or menthol compounds of formulas (II), (III) and/or (IV)

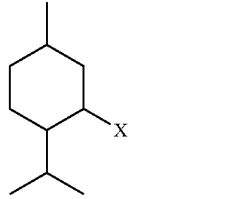

(II)

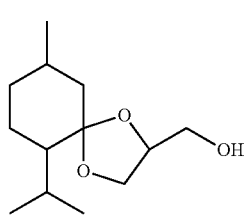

(III)

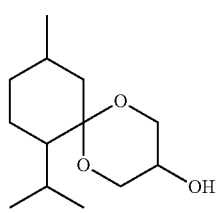

(IV)

wherein X denotes —OY or —COZ and Y denotes the following groups:
(i) a linear or branched alkyl or hydroxyalkyl residue with 1 to 6 carbon atoms or an allyl residue;
(ii) a hydroxy or dihydroxyalkyl residue with 1 to 6 carbon atoms;
(iii) an —$OCR^1$ residue;
(iv) an —OCO(M)OH residue;
(v) an —OCO—S residue;
(vi) an —$OC(CH_2)COR^2$ residue;
wherein
M denotes a linear or branched alkyl and/or alkenyl residue with 1 to 10, and preferably 1 to 4 carbon atoms;
S denotes a carbohydrate residue with 5 to 12 carbon atoms, and preferably a fructose, glucose, or sucrose residue;
n denotes 0 or numbers from 1 to 6, preferably 2 to 3;
$R^1$ denotes a linear or branched alkyl or hydroxyalkyl residue with 1 to 6, and preferably 1 to 2 carbon atoms, or an allyl residue;
$R^2$ denotes a hydroxyl residue or an —$NR^3 R^4$ residue;
$R^3$ and $R^4$, independently from each other, denote hydrogen or a linear or branched alkyl or hydroxyalkyl residue with 1 to 6, and preferably 1 to 2 carbon atoms,
while Z denotes the following groups:
(vii) an $NR^5 R^6$ residue or
(viii) an $NHR^7$ residue, wherein R[5] and R[6], independently from each other, denote hydrogen or a linear or branched alkyl or hydroxyalkyl residue with 1 to 6, and preferably 1 to 2 carbon atoms, or a phenyl residue or an alkoxyphenyl residue with 1 to 6, and preferably 1 to 2 carbon atoms in the alkoxy residue;

R[7] denotes a —(CH$_2$)$_n$COOR[8] residue;

R[8] denotes a linear or branched alkyl or hydroxyalkyl residue with 1 to 6, and preferably 1 to 2 carbon atoms, and n denotes 0 or numbers from 1 to 10, and preferably 1 to 4, or (b2) aromatic substances.

Surprisingly, it was found that mixtures of the amides, which are already known from WO 2012 061698, with menthol or menthol compounds of the above-described type not only have the action of synergistically increasing the cooling effect, but are also found by the consumer to taste better. The same applies for a combination of numerous aromatic substances.

In investigating the sensory properties of oral and dental care products, it was also noted that mixtures of special amides and menthol or menthol compounds synergistically reduce the solubility of hydroxyapatite and inhibit crystal growth, so that such preparations also counteract the demineralization of dental enamel and prevent tartar formation.

Amides

The amides that make up group (a) are known substances that can be manufactured by the relevant methods of organic chemistry. With respect to their manufacture, we refer in full to the contents of International Patent Application WO 2012 061698 A1, with the content disclosed therein hereby being incorporated by reference.

In this context, the two aryl or heteroaryl residues A[1] and A[2] in Formula (I) preferably correspond, independently of each other, to an optionally substituted phenyl, pyrrolyl, furanyl, thienyl, pyrazolyl, thiazolyl, isoxazolyl, isothiazoyl, pyridyl, pyrinidinyl, or triazinyl residue. These residues may be substituted once or twice with alkyl, heteroalkyl, alkenyl, alkoxy, hydroxyl, amino, N-dialkylamino, halogen, nitro, cyano, acyl, carbonyl, carboxyl esters or amide groups, wherein two substituents may optionally form an aliphatic or aromatic ring with a heteroatom of the aryl residue, giving rise to a bicyclic compound.

Group [B] preferably comprises an —OCH$_2$—, —OCH(CH$_3$)—, OCH(CH$_2$CH$_2$)$_3$—, —CH$_2$CH$_2$—, or —CH=CH— residue or is derived from cyclopropane, cyclobutane, or cyclopentane.

In another preferred embodiment, R$^a$ denotes an optionally substituted alkyl residue with 1 to 6 carbon atoms or an optionally substituted phenyl, pyrrolyl, furanyl, thienyl, pyrazolyl, thiazolyl, isoxazolyl, isothiazoyl, pyridyl, pyrinidinyl, or triazinyl residue, wherein the substitution pattern may correspond to that for A[1] and A[2].

Preferably, p denotes 2, while R$^b$, R$^c$, R$^d$, R$^e$, and R$^f$ all denote hydrogen. In order to avoid ambiguity, it is specified that the individual preferred structural elements are all preferred separately or may be combined as desired with one another to form particularly preferred embodiments. In the following, the particularly preferred embodiments are explained in further detail by means of Structural Formulas A1 to A214:

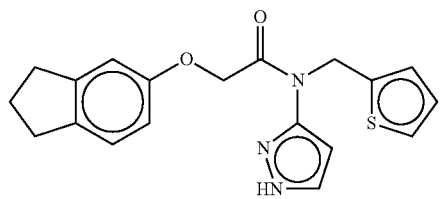

A1

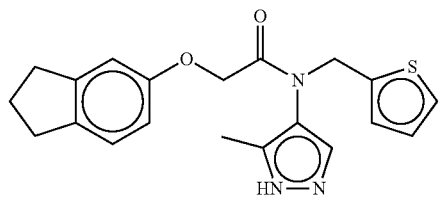

A2

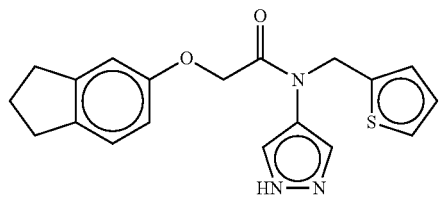

A3

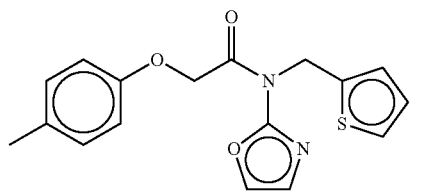

A4

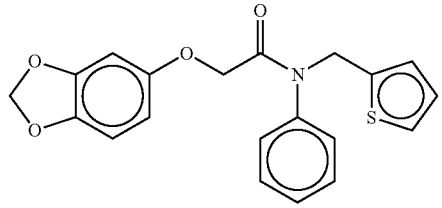

A5

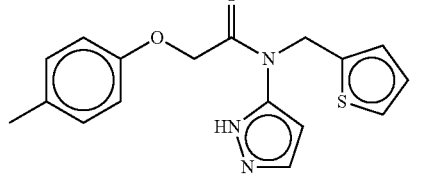

A6

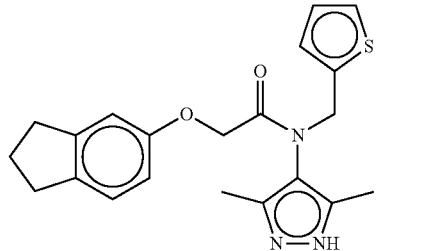

A7

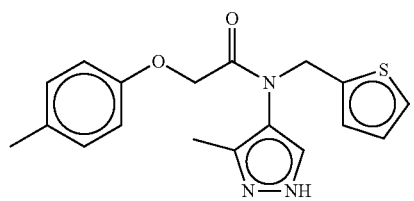
A8
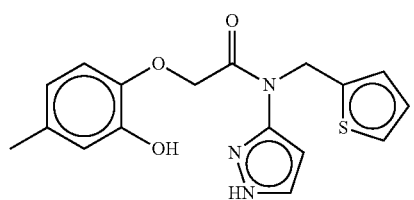
A9
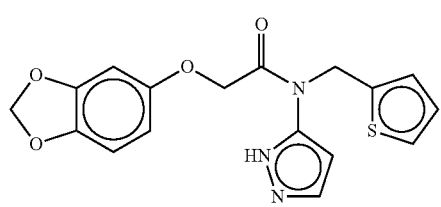
A10
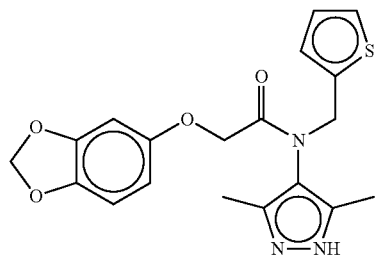
A11
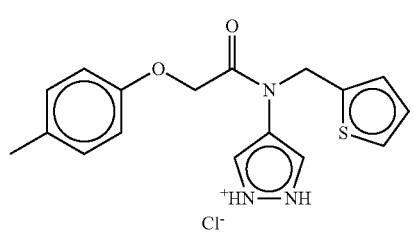
A12
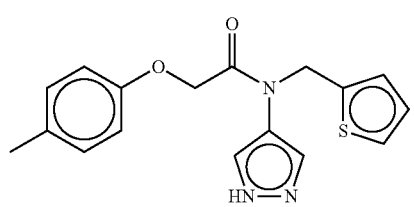
A13
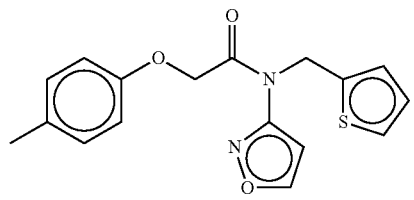
A14
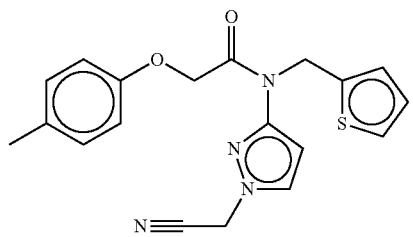
A15
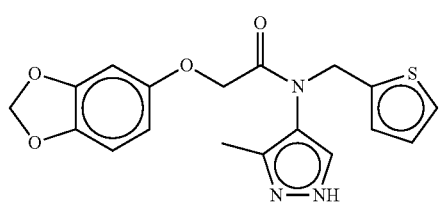
A16
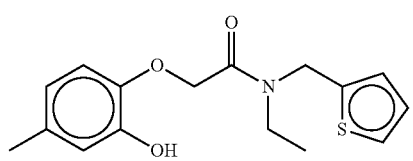
A17
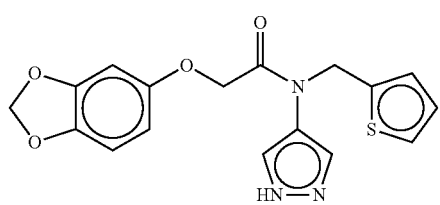
A18
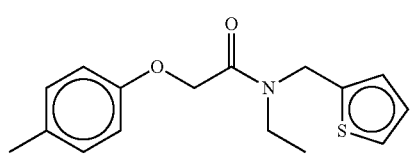
A19
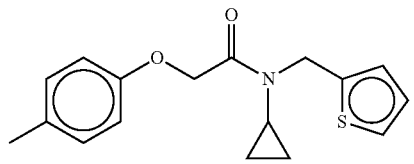
A20
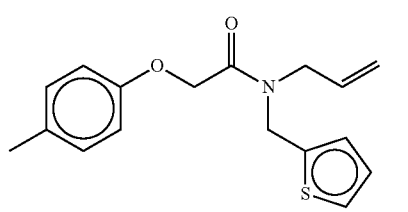
A21
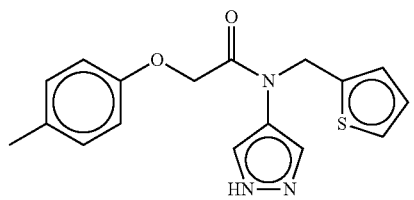
A22

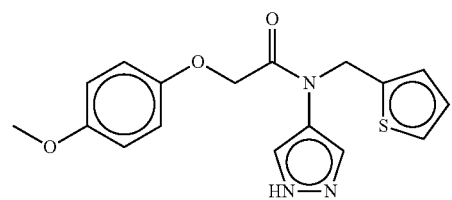 A23
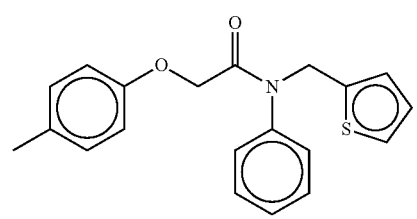 A24
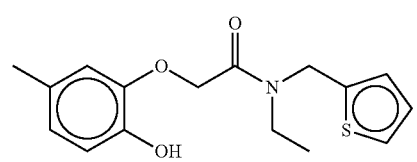 A25
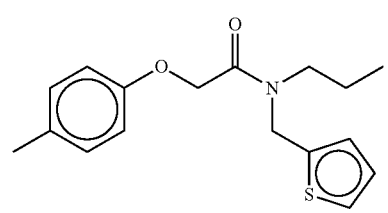 A26
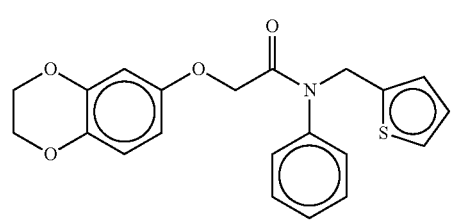 A27
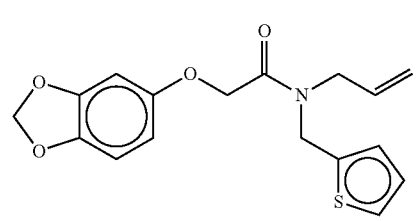 A28
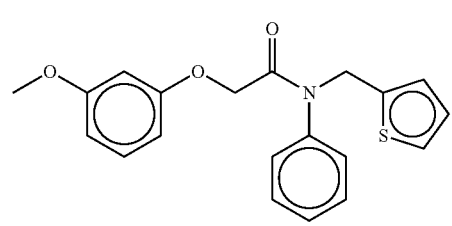 A29
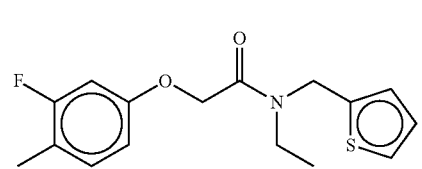 A30
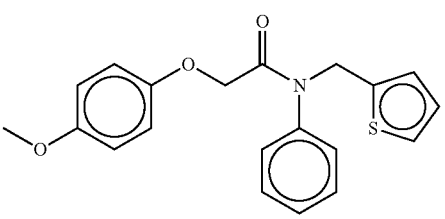 A31
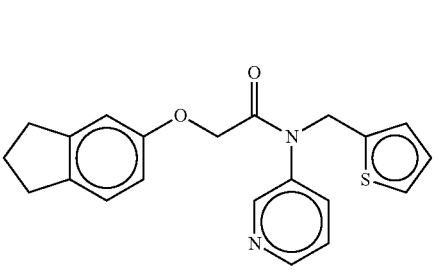 A32
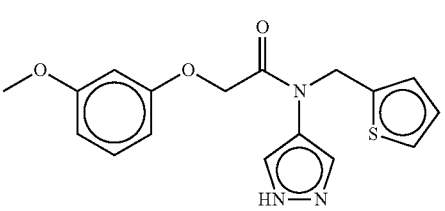 A33
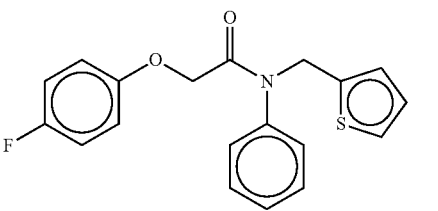 A34
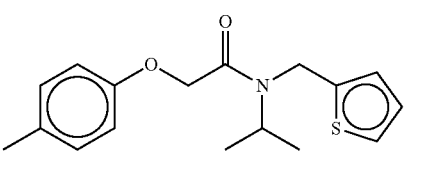 A35
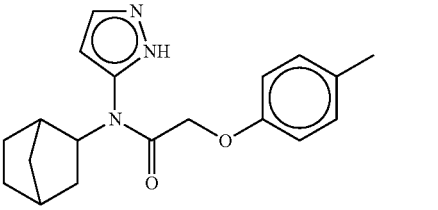 A36
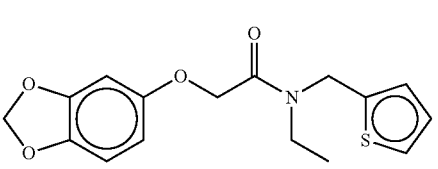 A37
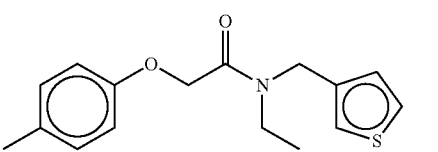 A38

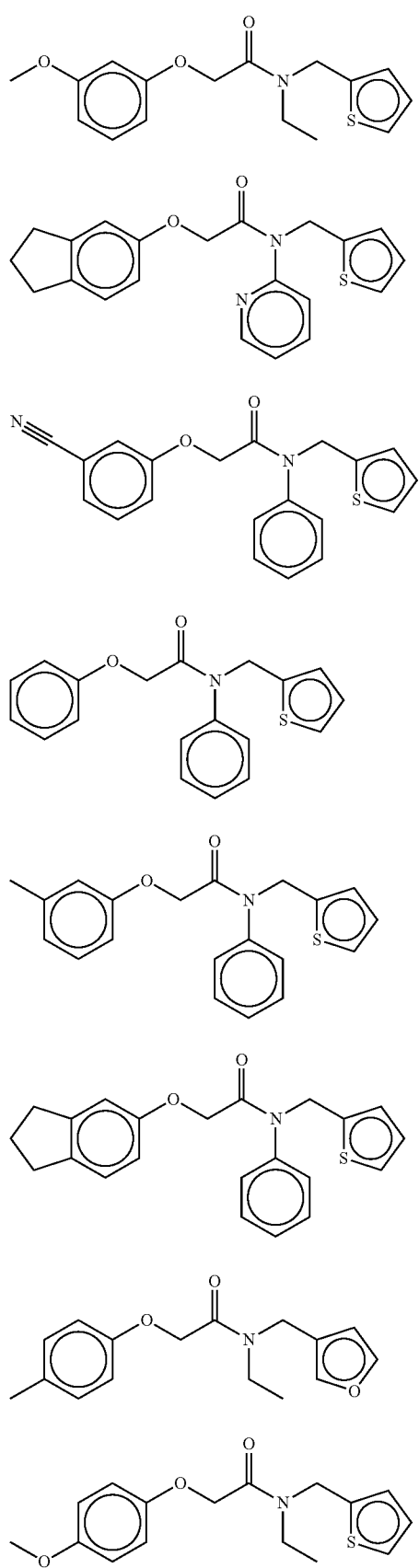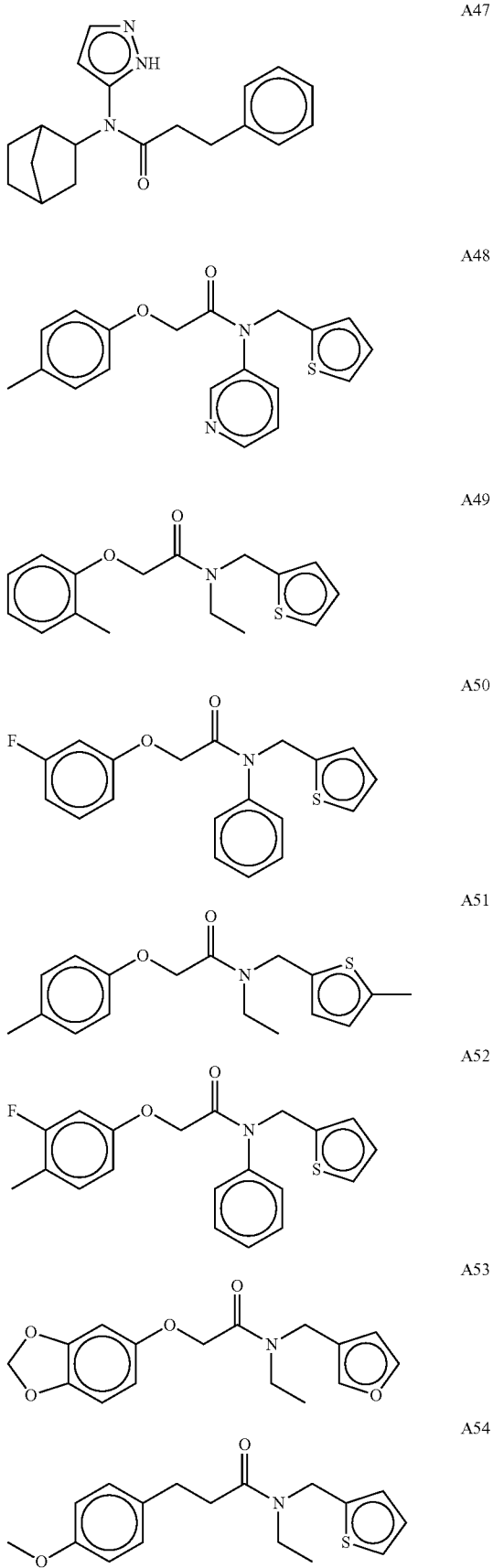

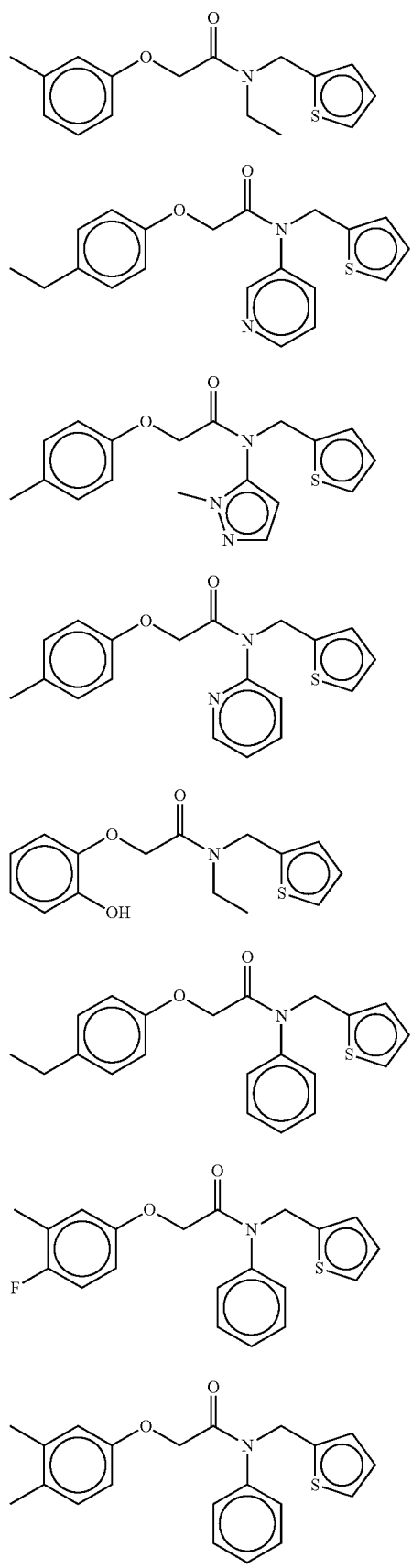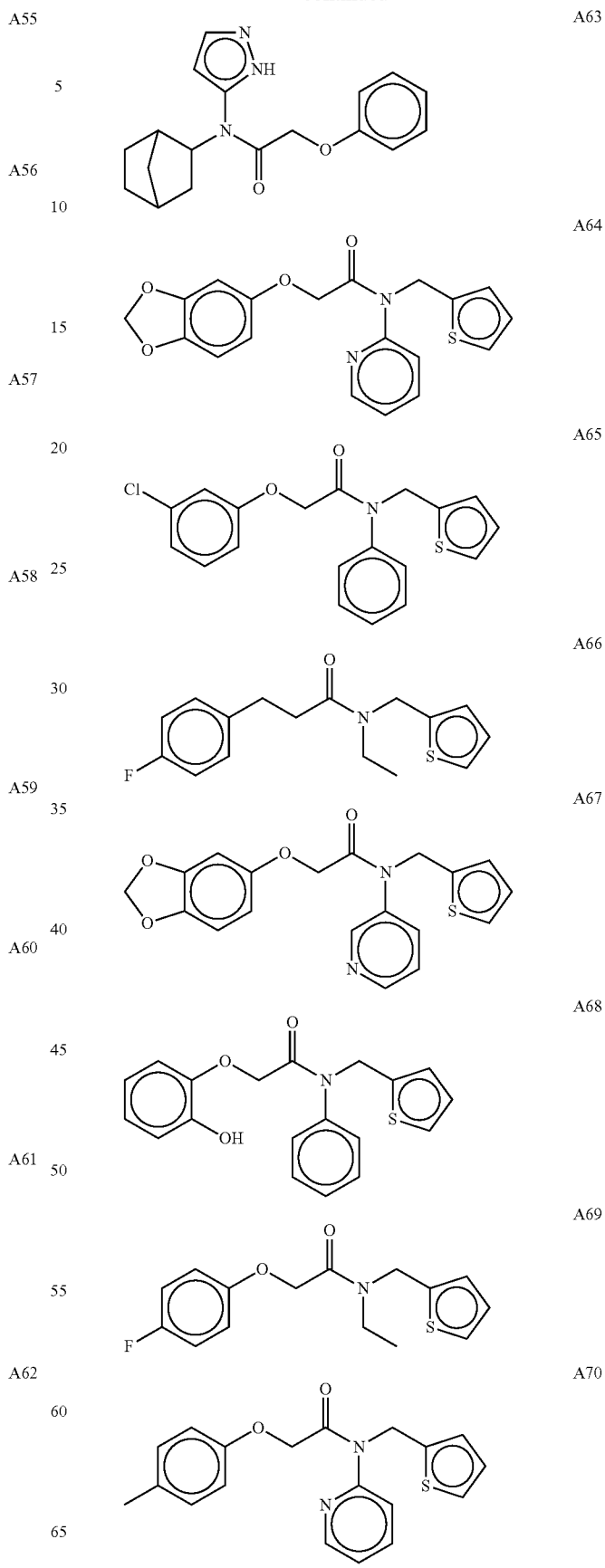

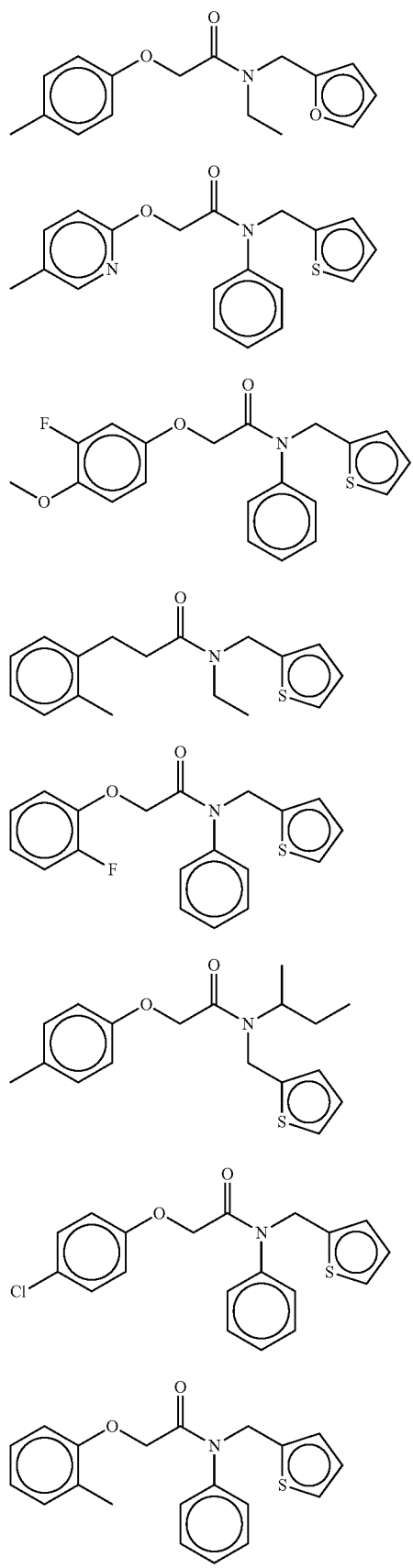

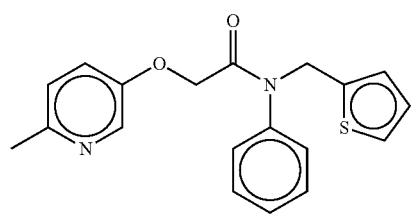 A87
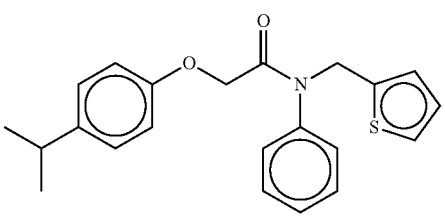 A94
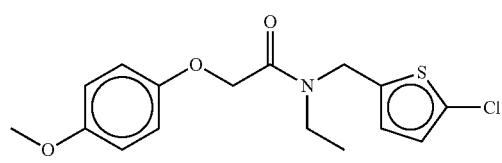 A88
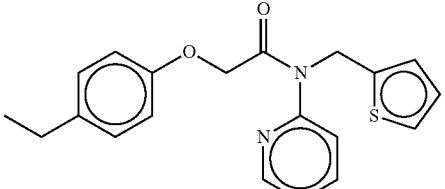 A95
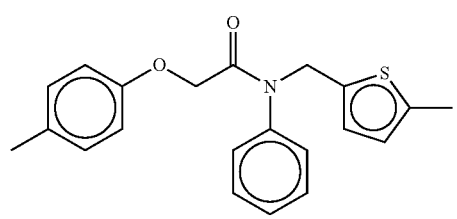 A89
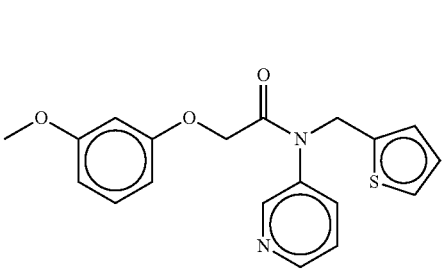 A96
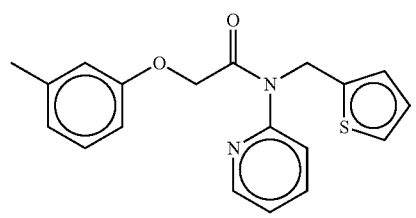 A90
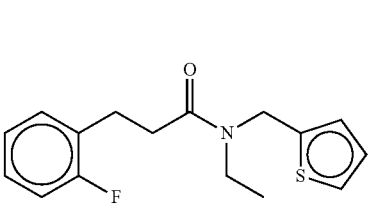 A97
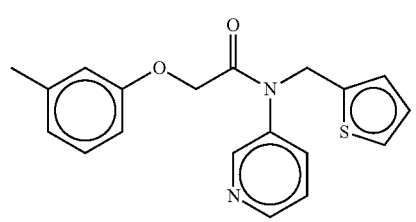 A91
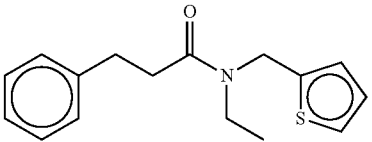 A98
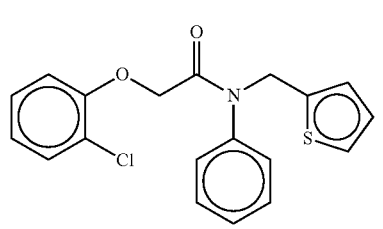 A92
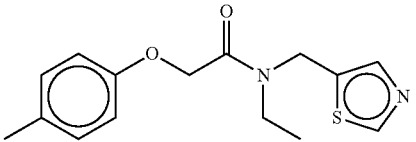 A99
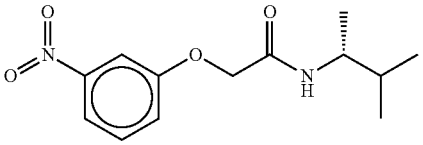 A100
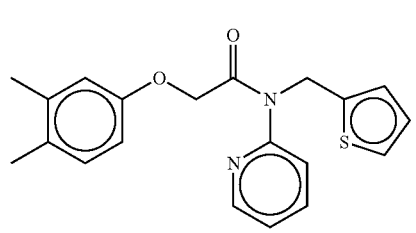 A93
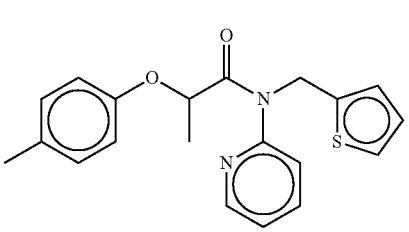 A101

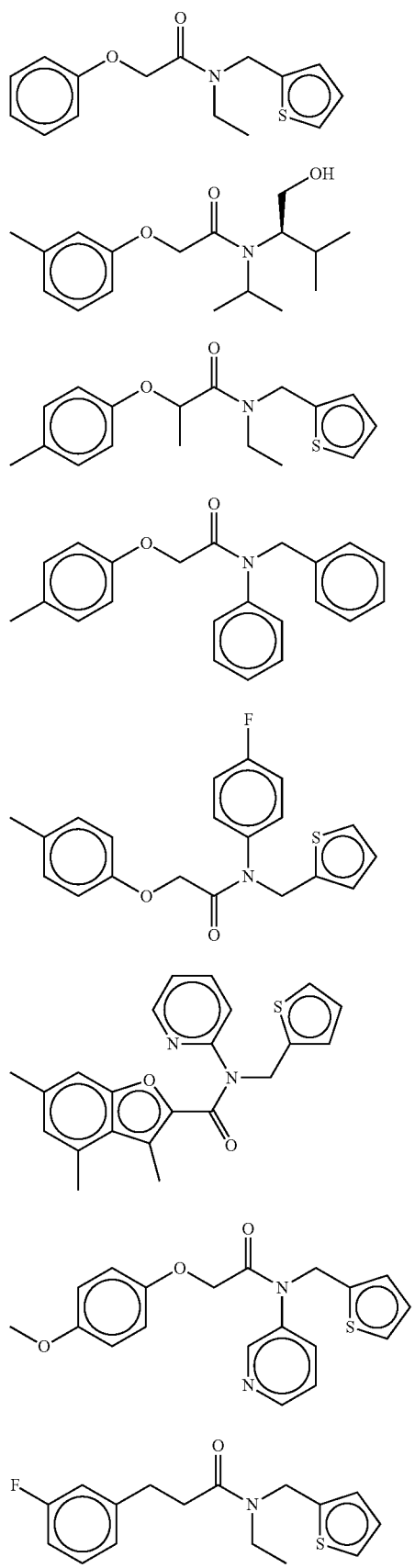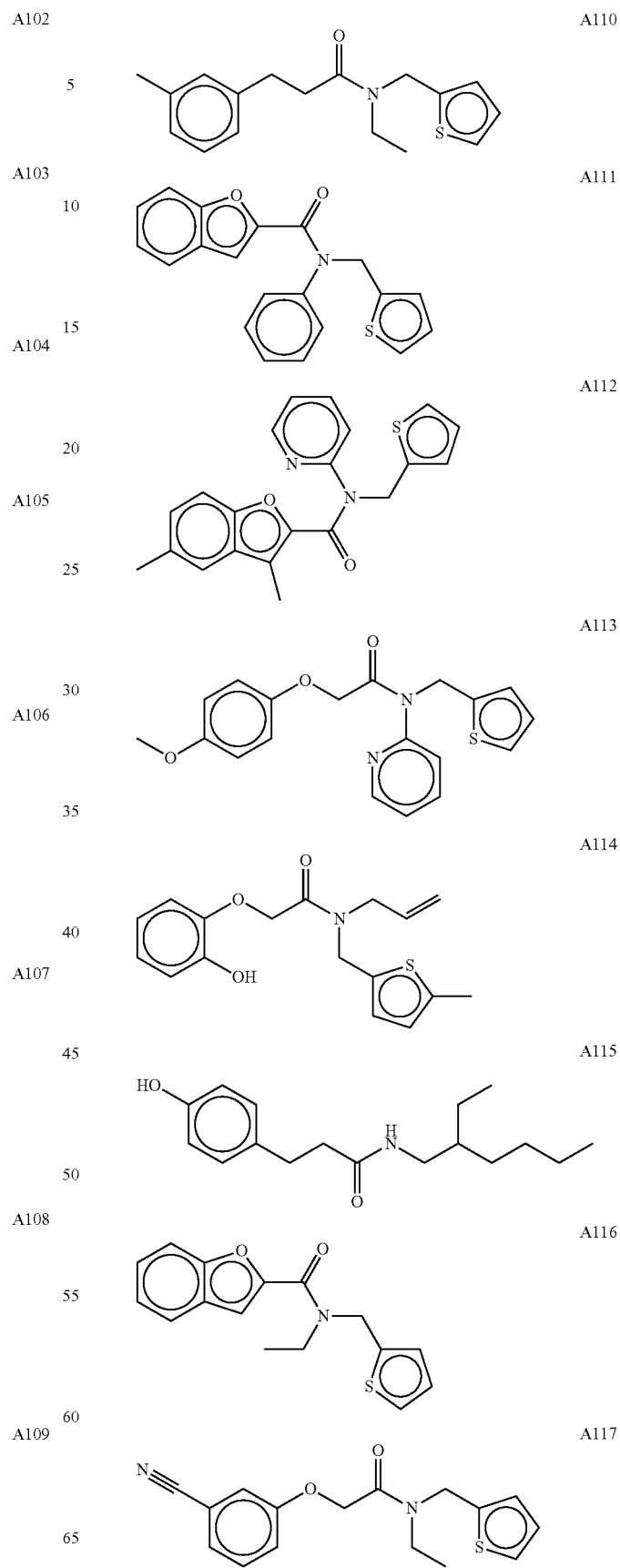

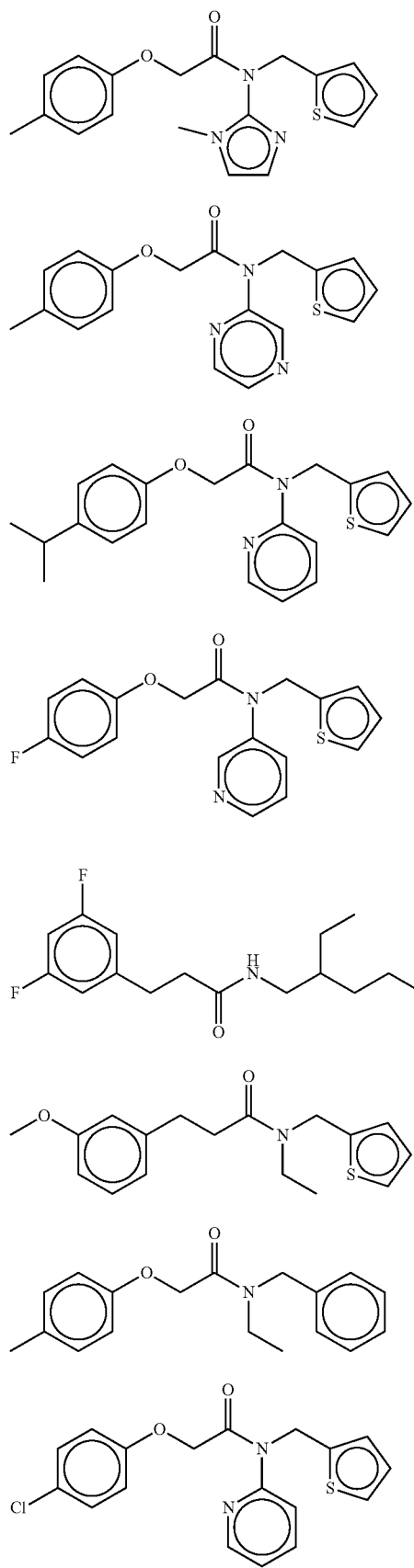

A134 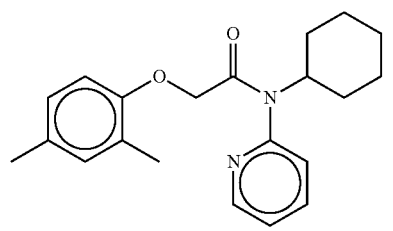
A135 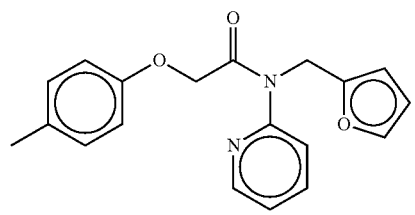
A136 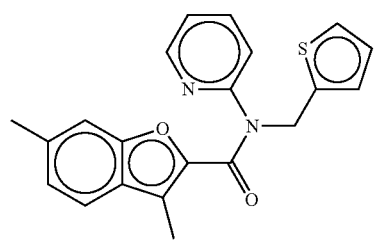
A137 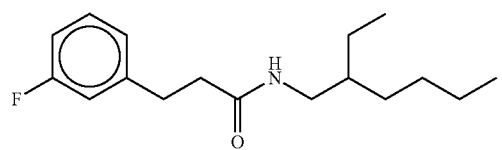
A138 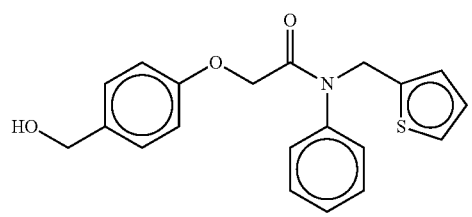
A139 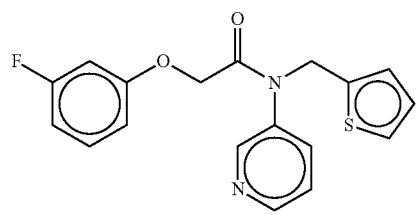
A140 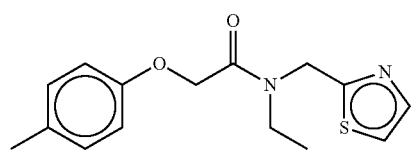
A141 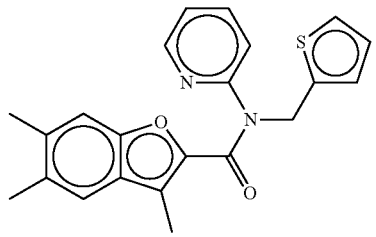
A142 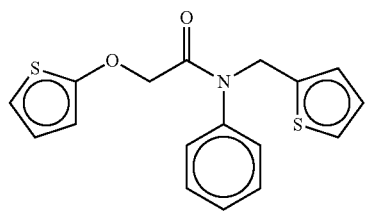
A143 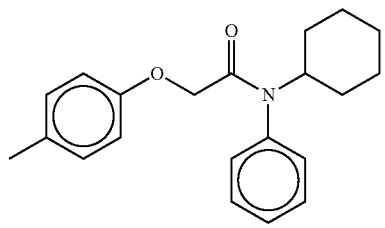
A144 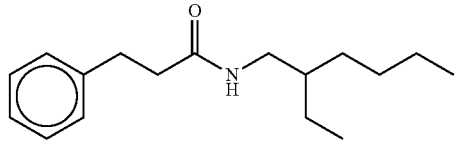
A145 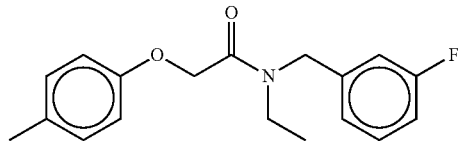
A146 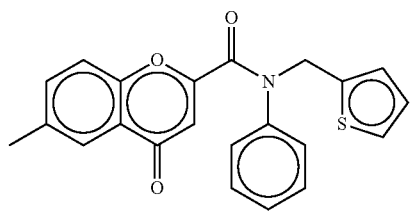
A147 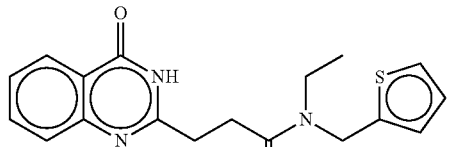
A148

A149 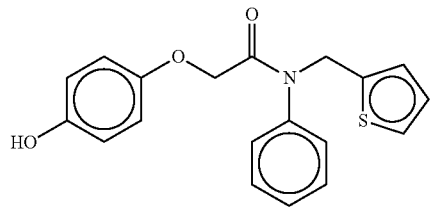
A150 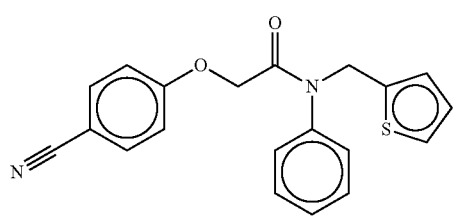
A151 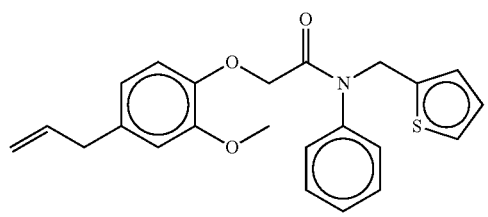
A152 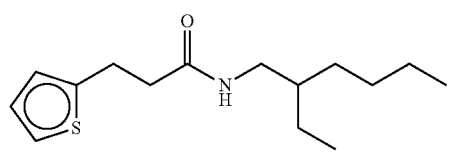
A153 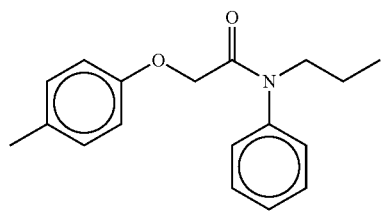
A154 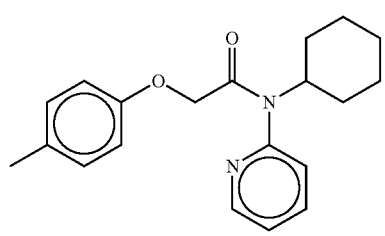
A155 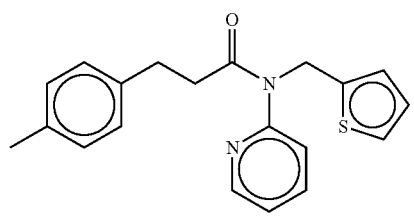
A156 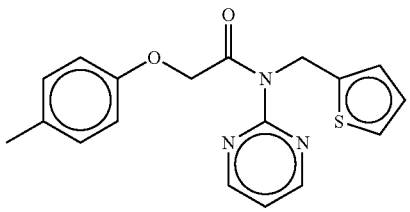
A157 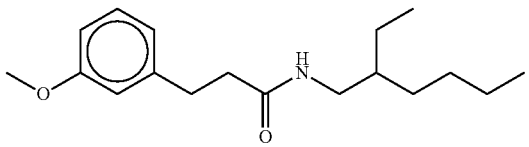
A158 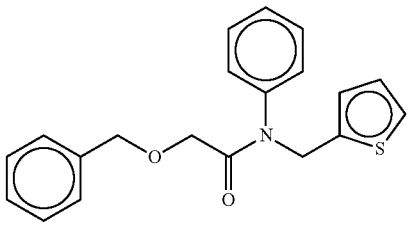
A159 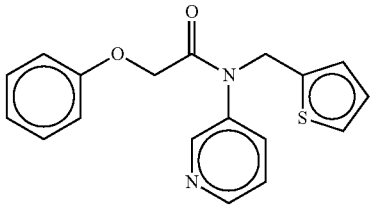
A160 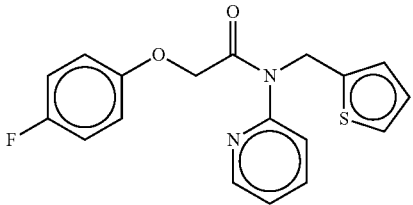
A161 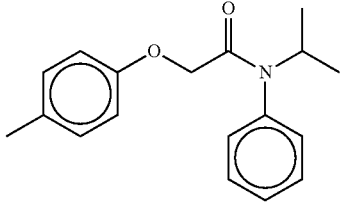
A162 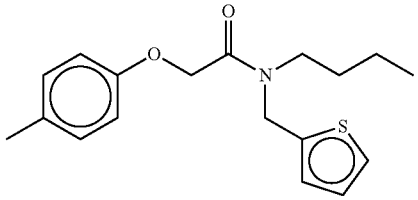

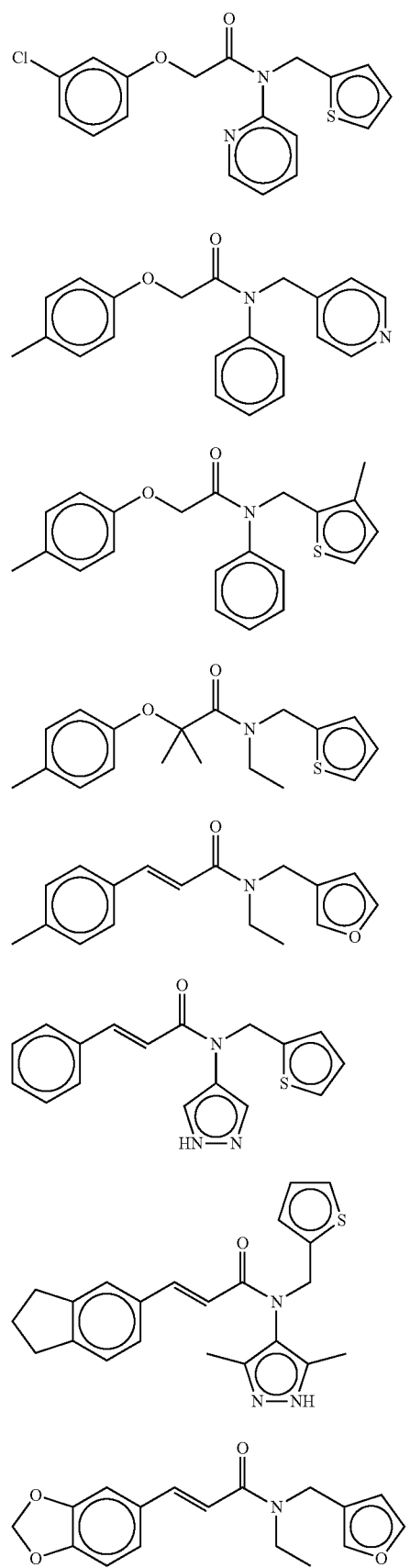

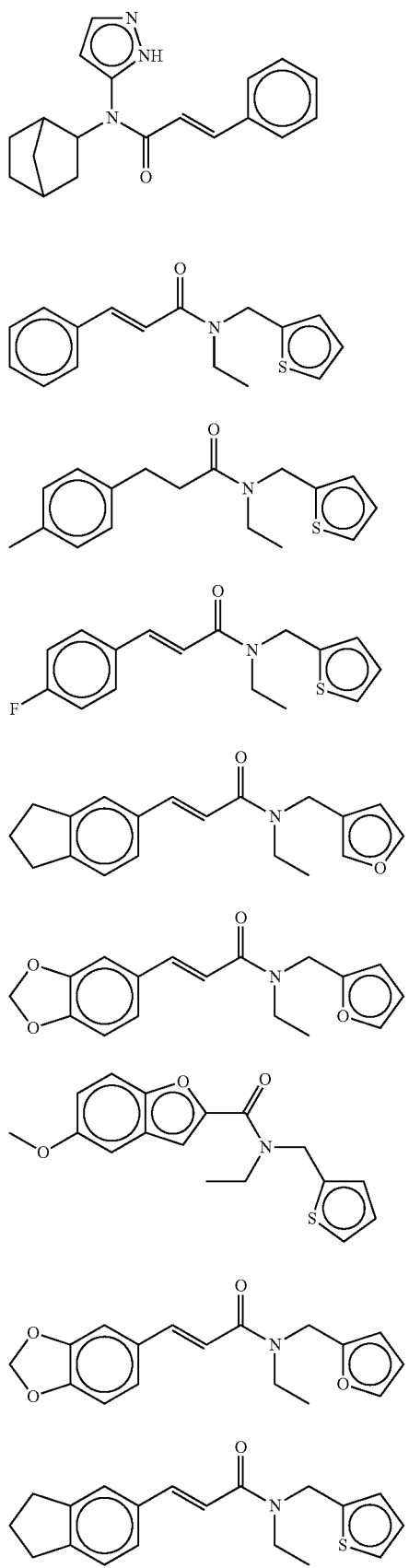
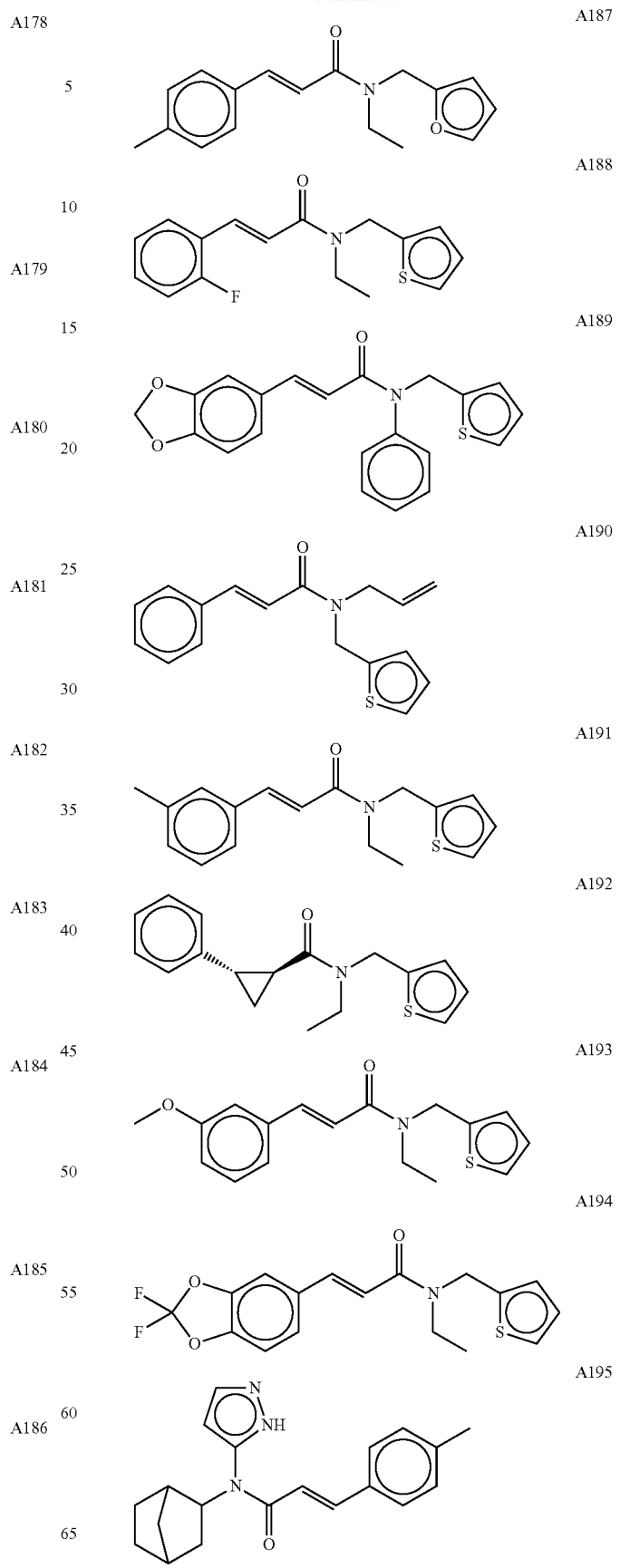

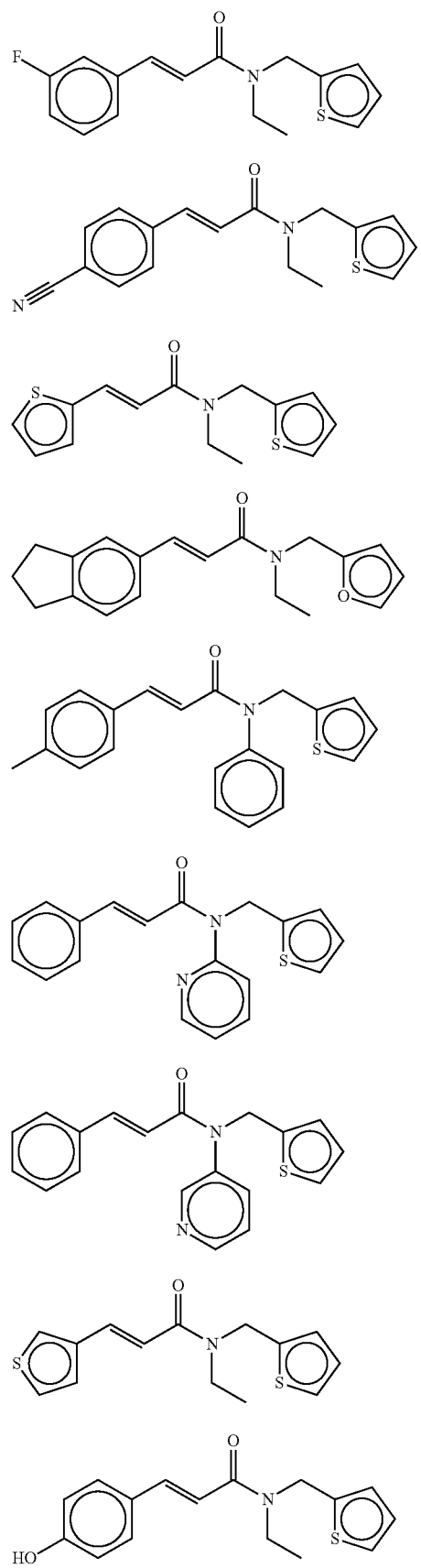
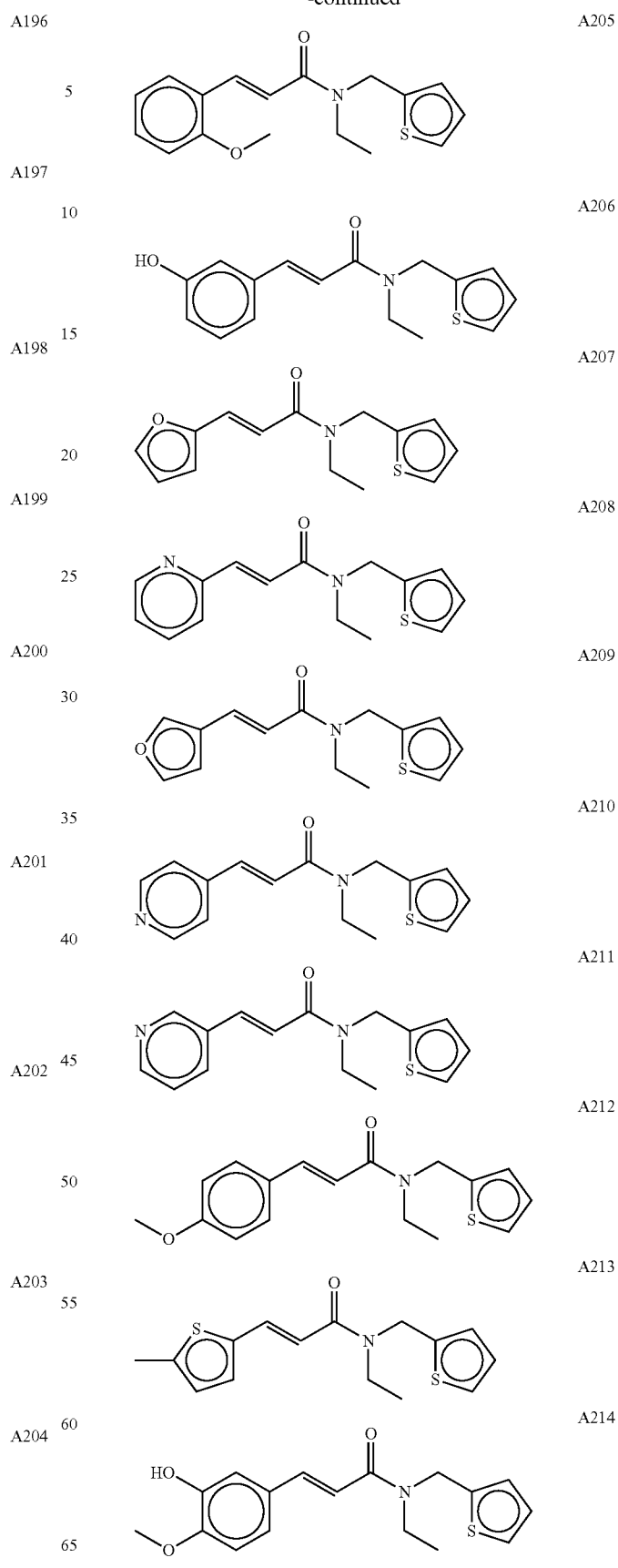

The following substances are particularly preferred:
N-(1H-pyrazol-5-yl)-N-(thiophen-2-ylmethyl)-2-(p-tolyloxy)acetamide;
N-ethyl-N-(thiophen-2-ylmethyl)-2-(p-tolyloxy)acetamide;
2-(p-tolyloxy)acetyl chloride;
N-(thiophen-2-ylmethyl)ethanamine;
2-(2,3-dihydro-1H-inden-5-yloxy)-N-(1H-pyrazol-3-yl)-N-(thiophen-2-ylmethyl)acetamide;
2-(2,3-dihydro-1H-inden-5-yloxy)-N-(4-methyl-1H-pyrazol-3-yl)-N-(thiophen-2-ylmethyl)acetamide;
2-(2,3-dihydro-1H-inden-5-yloxy)-N-(3,5-dimethyl-1H-pyrazol-4-yl)-N-(thiophen-2-ylmethyl)acetamide;
N-(3-methyl-1H-pyrazol-4-yl)-N-(thiophen-2-ylmethyl)-2-(p-tolyloxy)acetamide;
4-(N-(thiophen-2-ylmethyl)-2-(p-tolyloxy)acetamido)-1H-pyrazol-2-ium chloride;
N-(isoxazol-3-yl)-N-(thiophen-2-ylmethyl)-2-(p-tolyloxy)acetamide;
2-(benzo[d][1,3]dioxol-5-yloxy)-N-(3-methyl-1H-pyrazol-4-yl)-N-(thiophen-2-ylmethyl)acetamide;
2-(benzo[d][1,3]dioxol-5-yloxy)-N-(1H-pyrazol-4-yl)-N-(thiophen-2-ylmethyl)acetamide;
N-cyclopropyl-N-(thiophen-2-ylmethyl)-2-(p-tolyloxy)acetamide;
N-allyl-N-(thiophen-2-ylmethyl)-2-(p-tolyloxy)acetamide;
N-propyl-N-(thiophen-2-ylmethyl)-2-(p-tolyloxy)acetamide;
2-(3-methoxyphenoxy)-N-(1H-pyrazol-4-yl)-N-(thiophen-2-ylmethyl)acetamide;
N-(bicyclo[2.2.11]heptan-2-ylmethyl)-N-(1H-pyrazol-3-yl)-2-(p-tolyloxy)acetamide;
N-(bicyclo[2.2.1]heptan-2-ylmethyl)-N-(1H-pyrazol-3-yl)-2-(p-tolyloxy)acetamide;
N-(bicyclo[2.2.1]heptan-2-ylmethyl)-3-phenyl-N-(1H-pyrazol-3-yl) propanamide;
N-ethyl-N-((5-methylthiophen-2-yl)methyl)-2-(p-tolyloxy)acetamide;
N 2-(4-ethylphenoxy)-N-(pyridin-3-yl)-N-(thiophen-2-ylmethyl)acetamide;
N-(l-methyl-1H-pyrazol-5-yl)-N-(thiophen-2-ylmethyl)-2-(p-tolyloxy)acetamide;
N-(bicyclo[2.2.1]heptan-2-ylmethyl)-2-phenoxy-N-(1H-pyrazol-3-yl)acetamide;
N-sec-butyl-N-(thiophen-2-ylmethyl)-2-(p-tolyloxy)acetamide;
N-methyl-N-(thiophen-2-ylmethyl)-2-(p-tolyloxy)acetamide;
2-(3-methoxyphenoxy)-N-(pyridin-2-yl)-N-(thiophen-2-ylmethyl)acetamide;
2-(2-isopropyl-5-methylphenoxy)-N-(1H-pyrazol-3-yl)-N-(thiophen-2-ylmethyl)acetamide;
N-(pyridin-2-yl)-N-(thiophen-2-ylmethyl)-2-(m-tolyloxy)acetamide;
2-(4-ethylphenoxy)-N-(pyridin-2-yl)-N-(thiophen-2-ylmethyl)acetamide;
N-ethyl-N-(thiazol-5-ylmethyl)-2-(p-tolyloxy)acetamide;
((R)—N-(l-hydroxy-3-methylbutan-2-yl)-N-isopropyl-2-(m-tolyloxy)acetamide;
3,5-dimethyl-N-(pyridin-2-yl)-N-(thiophen-2-ylmethyl)benzofuran-2-carboxamide;
N-(pyrazin-2-yl)-N-(thiophen-2-yl methyl)-2-(p-tolyloxy)acetamide;
N-benzyl-N-ethyl-2-(p-tolyloxy)acetamide;
2-(2-isopropyl-5-methylcyclohexyloxy)-N-(2-(pyridin-4-yl)ethyl)acetamide;
N-(furan-2-yl methyl)-N-(pyridin-2-yl)-2-(p-tolyloxy)acetamide;
N-ethyl-N-(thiazol-2-ylmethyl)-2-(p-tolyloxy)acetamide;
3,5,6-trimethyl-N-(pyridin-2-yl)-N-(thiophen-2-ylmethyl)benzofuran-2-carboxamide;
N-((5-ethylthiophen-2-yl)methyl)-N-phenyl-2-(p-tolyloxy)acetamide;
2-phenoxy-N-(pyridin-3-yl)-N-(thiophen-2-ylmethyl)acetamide;
2-(3-chlorophenoxy)-N-(pyridin-2-yl)-N-(thiophen-2-ylmethyl)acetamide;
N-((3-methylthiophen-2-yl)methyl)-N-phenyl-2-(p-tolyloxy)acetamide;
(E)-N—(S-methyl-1H-pyrazol-4-yl)-N-(thiophen-2-ylmethyl)-3-p-tolylacrylamide;
(E)-N-(1H-pyrazol-4-yl)-N-(thiophen-2-ylmethyl)-3-p-tolylacrylamide;
(E)-3-p-tolylacryloyl chloride;
(E)-3-(benzo[d][1,3]dioxol-5-yl)-N-(1H-pyrazol-4-yl)-N-(thiophen-2-ylmethyl)acrylamide;
(E)-N-(3,5-dimethyl-1H-pyrazol-4-yl)-N-(thiophen-2-ylmethyl)-3-p-tolylacrylamide;
(E)-3-(benzo[d][1,3]dioxol-5-yl)-N-ethyl-N-(thiophen-2-ylmethyl)acrylamide;
(E)-3-(4-methoxyphenyl)-N-(1H-pyrazol-4-yl)-N-(thiophen-2-ylmethyl)acrylamide;
N-(3,5-dimethyl-1H-pyrazol-4-yl)-N-(thiophen-2-ylmethyl) cinnamamide;
N-(1H-pyrazol-4-yl)-N-(thiophen-2-ylmethyl)cinnamamide;
(E)-3-(2,3-dihydro-1H-inden-5-yl)-N-(3,5-dimethyl-1H-pyrazol-4-yl)-N-(thiophen-2-ylmethyl)acrylamide;
(+/−)(E)-2-phenyl-N-(1H-pyrazol-4-yl)-N-(thiophen-2-ylmethyl)cyclopropanecarboxamide
(E)-3-(2,3-dihydro-1H-inden-5-yl)-N-(1H-pyrazol-5-yl)-N-(thiophen-2-ylmethyl)acrylamide;
N-ethyl-N-(thiophen-2-ylmethyl)cinnamamide;
2-(2,3-dihydro-1H-inden-5-yloxy)-N-ethyl-N-(thiazol-5-ylmethyl)acetamide;
2-(2,3-dihydro-1H-inden-5-yloxy)-N-ethyl-N-(thiazol-5-ylmethyl)acetamide;
(+/−)(E)-N-ethyl-2-phenyl-N-(thiophen-2-yl methyl)cyclopropanecarboxamide;
N-(bicyclo[2.2.1]heptan-2-yl)-2-(2,3-dihydro-H-inden-5-yloxy)-N-(1H-pyrazol-1-yl) acetamide;
N-(bicyclo[2.2.1]heptan-2-yl)-2-(cyclohexyloxy)-N-(1H-pyrazol-5-yl)acetamide;
2-(2,3-dihydro-1H-inden-5-yloxy)-N-ethyl-N-((5-methylthiophen-2-yl)methyl)acetamide;
(E)-N-phenyl-N-(thiophen-2-ylmethyl)-3-p-tolylacrylamide;
(+1-) (E)-N,2-diphenyl-N-(thiophen-2-ylmethyl)cyclopropanecarboxamide;
3,5-dimethyl-N-(pyridin-2-yl)-N-(thiophen-2-ylmethyl)benzofuran-2-carboxamide;
(E)-N-allyl-3-(7-chlorobenzo[d][1,3]dioxol-5-yl)-N-(thiophen-2-ylmethyl)acrylamide;
(E)-N-ethyl-3-(4-(imidazo[1,2-a]pyridin-2-ylmethoxy)phenyl)-N-(thiophen-2-ylmethyl)acrylamide;
N-(cyclohexylmethyl)-N-ethyl-2-(p-tolyloxy)acetamide;
Menthol and Menthol Compounds Menthol compounds, which can be used within the meaning of the invention and form group (b1), may be selected—in addition to the basic substance menthol itself—for example from the group composed of menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamate, monomethyl succinate (FEMA GRAS 3810), monomenthyl glutamate (FEMA GRAS 4006), menthoxy-1,2-propanediol (FEMA GRAS 3784), menthoxy-2-methyl-1,2-propanediol (FEMA GRAS 3849), the menthane carboxylic acid esters and amides WS-3, WS-4, WS-5, WS-12, WS-14, and WS-30, as well as mixtures thereof.

A first important representative of the substances constituting component (b) is monomenthyl succinate (FEMA GRAS 3810), which was patented as a substance as early as 1963 by Brown & Williamson Tobacco Corp. (U.S. Pat. No. 3,111,127), and as a cooling agent is the object of U.S. Pat. Nos. 5,725,865 and 5,843,466 (V. Mane Fils). Both the succinate and the analog monomenthyl glutarate (FEMA GRAS 4006) constitute important representatives of monomenthyl esters based on di- and polycarboxylic acids:

[1] FEMA stands for "Flavor and Extracts Manufacturers Association", and GRAS is defined as Generally Regarded As Safe". A FEMA GRAS rating means that the substance so designated has been tested according to standard methods and is considered to be toxicologically harmless.

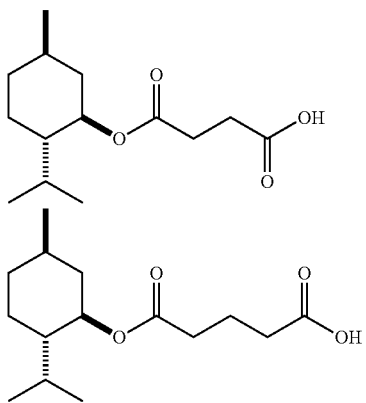

Examples of applications of these substances can be found e.g. in the documents WO 2003 043431 (Unilever) or EP 1332772 A1 (IFF).

The next important group of preferred menthol compounds according to the invention comprises carbonate esters of menthol and polyols, such as e.g. glycols, glycerol, or carbohydrates, such as e.g. menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849), or the corresponding sugar derivatives:

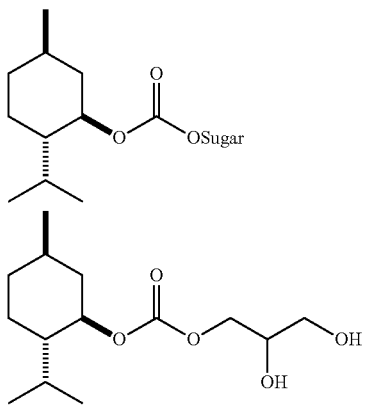

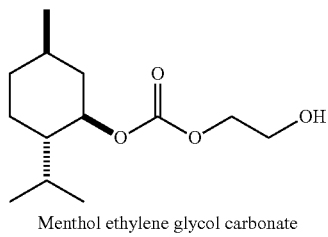

Menthol ethylene glycol carbonate

The use of such substances as cooling agents for cigarettes is the object, for example, of the document U.S. Pat. No. 3,419,543 (Mold et al.) from 1968; use as a physiological cooling agent is claimed in DE 4226043 A1 (H&R).

According to the invention, preferred menthol compounds are menthyl lactate (FEMA GRAS 3748=Frescolat® ML), and in particular menthone glyceryl acetal (FEMA GRAS 3807) or menthone glyceryl ketal (FEMA GRAS 3808), which is marketed under the name Frescolat® MGA.

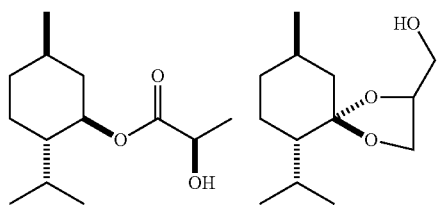

The former structure is obtained by esterification of lactic acid with menthol, and the latter by acetalization of menthone with glycerol (cf. DE 2608226 A1, H&R). Another member of this group of compounds is 3-(l-menthoxy)-1,2, propanediol, also known as Cooling Agent 10 (FEMA GRAS 3784, cf. U.S. Pat. No. 6,328,982, TIC), as well as 3-(l-menthoxy)-2-methyl-1,2,propanediol (FEMA GRAS 3849), which has an additional methyl group.

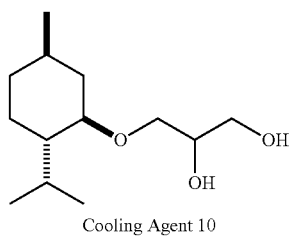

Cooling Agent 10

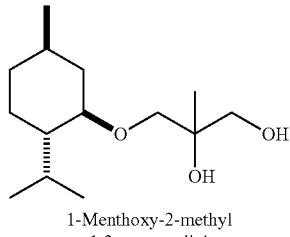

1-Menthoxy-2-methyl
1,2-propanediol

Manufacturing of 3-(l-menthoxy)-1,2,propanediol is conducted, for example, starting from menthol according to the following diagram (cf. U.S. Pat. No. 4,459,425, Takagaso):

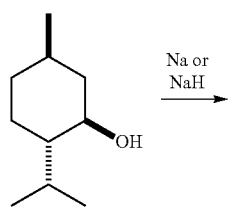

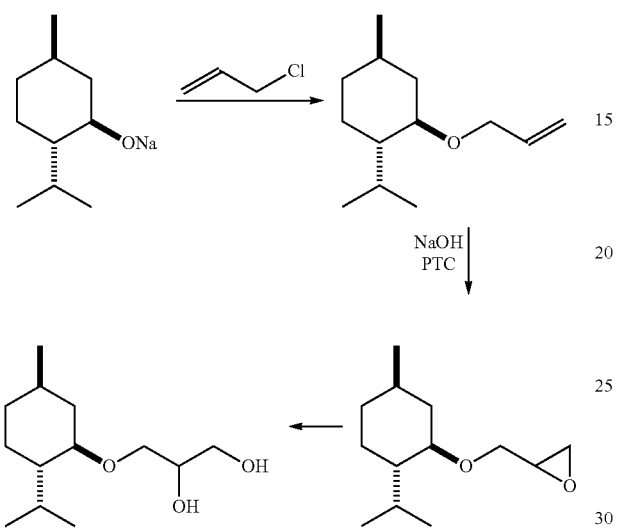

Alternative routes, in which menthol is reacted with epichlorohydrin in the first step, are described in U.S. Pat. Nos. 6,407,293 and 6,515,188 (Takagaso). An overview of the preferred menthol compounds, which are characterized by a CO bond, is given below:

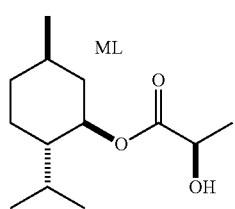

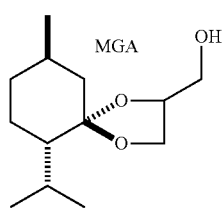

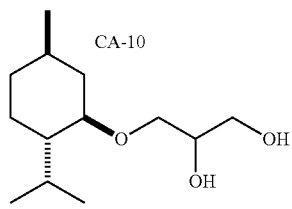

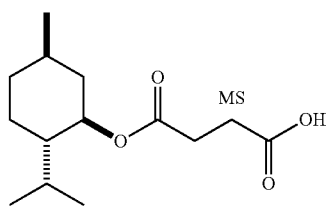

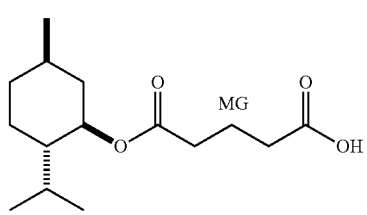

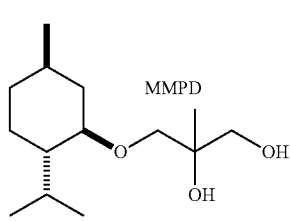

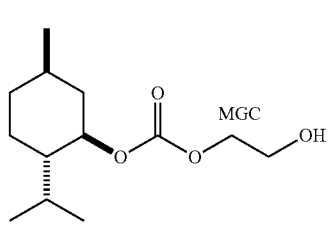

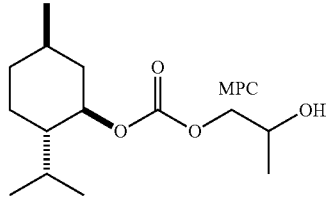

Among these substances, menthone glyceryl acetal/ketal, menthyl lactate, and menthol ethylene glycol carbonate or menthol propylene glycol carbonate, which are marketed by the Applicant under the names Frescolat® MGA, Frescolat® ML, Frescolat® MGC and Frescolat® MPC, have been shown to be quite particularly advantageous.

In the past century, menthol compounds having a C—C bond at position 3 were first developed in the 1970s, and a number of representatives of such compounds can also be used according to the invention. These substances are generally referred to as being of the WS type. The basic substance is a menthol derivative in which the hydroxyl is replaced by a carboxyl group (WS-1). All further WS types are derived from this structure, such as e.g. the species, also preferred according to the invention, of WS-3, WS-4, WS-5, WS-12, WS-14 and WS-30. The two diagrams below show the synthesis routes:

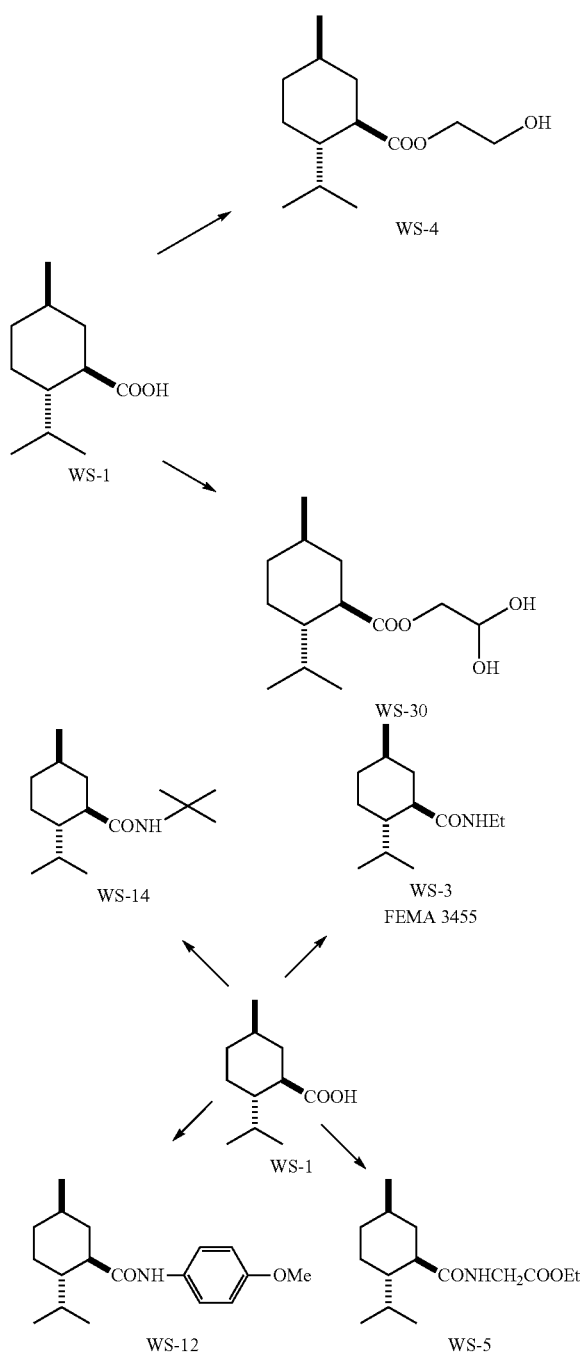

For example, the esters derived from WS-1 are described in U.S. Pat. No. 4,157,384, and the corresponding N-substituted amides are described in J. Soc. Cosmet. Chem. S. 185-200 (1978).

Aromatic Substances

The aromatic substances that form the component (b2) are selected from the group composed of anethol, acetanisole, acetaldehyde, acetylmethylcarbinol, 2-acetylpyrazine, 2-acetylpyridine, 2-acetylthiazoline, 2-acetylthiazole, allyl capronate, alpha-amylcinnamaldehyde, para-anisaldehyde, anis alcohol, dimethyl isopropyldithiazine, benzaldehyde, benzyl acetate, L-borneol, butyric acid, butyl acetate, 3-butylidene phthalide, capronic acid, carvacrol, L-carvone, d-carvone, carvomenthone, cis-carvyl acetate, caryophyllene, 1,8-cineol, 1,4-cineol, cinnamyl acetate, citral, citronellal, citronellol, citronellyl acetate, cumin aldehyde, cyclopentadecanolide, alpha-damascone, beta-damascone, alpha-damascenone, beta-damascenone, delta-decalactone, gamma-decalactone, dehydromenthofurolactone, dihydromenthofurolactone, 2,3-diethylpyrazine, dihydroanethol, dihydrocarvone, dihydrocumarin, beta-dihydroionone, dimethyl anthranilate, dimethyl sulfide, dimethyl pyrazine, sotolone, diphenyl oxide, divanillin, 2,4-decadienal, delta-dodecalactone, gamma-dodecalactone, acetic acid, ethyl acetate, ethyl butyrate, ethyl 2-methylbutyrate, ethyl capronate, ethyl caprylate, ethyl cinnamate, ethyl isobutyrate, ethyl vanillin, ethyl lactate, ethyl maltol, ethyl methylthiopropionate, 4-ethylphenol, ethyl isovalerianate, eugenol, fenchol, furaneol, filbertone, frambinone, frambinone methylether, furfurylthiol, undecatriene, geraniol, geranyl acetate, geranyl isobutyrate, guaiacol, heliotropin, 2-heptanone, Z-4-heptenal, gamma-hexalactone, gamma-heptalactone, Z-3-hexenol, E-2-hexenol, hexanol, hexyl acetate, Z-3-hexenyl acetate, E-2-hexenyl acetate, alpha-hexyl cinnamaldehyde, Z-3-hexenyl capronate, hotrienol, indole, alpha-iron, alpha-ionone, beta-ionone, isoamyl acetate, isoamyl butyrate, isoamyl isovaerianate, isobutyl acetate, isobutyl thiazole, isobutyraldehyde, isovaleraldehyde, isoeugenol, isomenthone, isopropyl methoxypyrazine, isobutyl methoxypyrazine, 2,4-isopropyl methylpyrazine, isopulegol, jasmine lactone, cis-jasmone, camphor, ketoisophorone, cresole, d-limonene, L-linalool, D-linalool, linalyl acetate, linalool oxide, maltol, methylcyclopentenolone, L-menthone, D-menthone, L-menthol, D-menthol, neomenthol, L-menthyl acetate, D-menthyl acetate, massoia lactone, melonal, 1,8-menthene thiol, 1,8-epithiomenthane, 8,3-thiomenthanone, menthofurolactone, menthadienyl acetate, 2,3-methoxymethylpyrazine, methyl anthranilate, methyl salicylate, thymol, methyl butyrate, 2-methyl butylacetate, methyl cinnamate, 2,3-methylfuranthiol, 2,3-methyltetrahydrofuran thiol, methyl jasmonate, methyl dihydrojasmonate, methyl thiobutyrate, 1,3-methylthiohexylacetate, 1,3-methylthiohexanol, methional, myrtenal, naringin, neral, nerol, neryl acetate, gamma-nonalactone, delta-nonalactone, E-2-nonenal, Z-6-nonenal, Z-6-nonenol, nootkatone, dihydronootkatone, 1,3-octenol, gamma-octalactone, delta-octalactone, pellitorine, 1,3-pentenone, pentyl acetate, phenylacetaldehyde, phenylethyl alcohol, phenylethyl acetate, piperitanate, prenyl thiol, prenyl thioacetate, rose oxide, rubenamine, rubescenamine, sabinene hydrate, skatole, styrolyl acetate, terpineol, 4-terpinenol, 1,3-thiohexanol, 1,3-thiohexyl acetate, 4,4,2-thiopentanone, trimethylpyrazine, gamma and delta-undecalactone, 2,4-decadienal, 2,4-nonadienal, 2,6-nonadienal, 2,4-undecadienal, vanillin, vinyl guaiacol, whisky lactone, cinnamaldehyde, cinnamyl alcohol, diallyl disulfide, allyl isothiocyanate, hexanal, E-2-hexenal, octanal, decanal, tridecatrienal, 12-methyltridecanal, alpha-pinene, beta-pinene, and piperitone, as well as mixtures thereof.

In another preferred embodiment of the invention, the preparations may comprise as component (c) cosmetic additives selected from the group consisting of surfactants, oil components, emulsifiers, pearlescent waxes, consistency-enhancing agents, thickeners, superfatting agents, stabilizers, polymers, silicone compounds, fats, waxes, lecithins, phospholipids, UV light protection factors, humectants, biogenic agents, antioxidants, deodorants, antiperspirants, anti-dandruff agents, film-forming agents, swelling agents, insect repellents, self-tanning agents, tyrosine inhibitors (depigmentation agents), hydrotropes, solubilizers, preservatives, perfumed oils and dyes, as well as mixtures thereof. Such preparations, particularly if they are in the form of emulsions, are characterized by improved shelf life.

The preparations according to the invention may comprise components (a) and (b) in a ratio by weight of 0.1:99 to 99.9:1, preferably 10:90 to 90:10, more preferably 25:75 to 75:25, and particularly preferably 40:60 to 60:40. The components (a+b) and (c) may be contained in a ratio by weight of 0.01:99.9 to 2:98, preferably 0.5:99.5 to 1.5:98.5, and particularly preferably about 1:99.

INDUSTRIAL APPLICABILITY

Cosmetic and/or Pharmaceutical Preparations

A further object of the present invention concerns cosmetic preparations, comprising
(a) amides of formula (I),
(b) menthol and/or menthol compounds of formulas (II), (III) and/or (IV) or aromatic substances, as well as
(c) a carrier approved for cosmetic use.

The cosmetic products should preferably be skin care products, hair care products, body care products, sunscreen products, as well as oral and dental care products. Particularly preferred are preparations in the form of emulsions, microemulsions or PIT emulsions.

A further object of the present invention concerns pharmaceutical preparations, comprising
(a) amides of formula (I),
(b) menthol and/or menthol compounds of formulas (II), (III) and/or (IV) or aromatic substances, as well as
(c) a carrier approved for pharmaceutical use
for the treatment of colds, wherein the characteristic of the invention is that it is used for therapeutic purposes.

The pharmaceutical products should preferably be lozenges, cold medication in candy form, cold syrups, cold ointments and cold sprays.

In this case, the cosmetic or pharmaceutical carriers should preferably be selected from the group composed of water, alcohols with 2 to 6 carbon atoms, polyols with 1 to 10 carbon atoms and 2 to 4 hydroxyl groups, and oil components. In addition to water, particularly preferred carriers are ethanol, isopropyl alcohol, ethylene glycol, propylene glycol, glycerol, trimethylol propane, pentaerythritol, and esters of linear or branched, saturated and particularly unsaturated fatty acids with 6 to 22, and preferably 8 to 18 carbon atoms, and alcohols with 1 to 6 carbon atoms.

The cosmetic and/or pharmaceutical preparations according to the invention may contain components (a) and (b) in a ratio by weight of 0.1:99 to 99.9:1, preferably 10:90 to 90:10, more preferably 25:75 to 75:25, and particularly preferably 40:60 to 60:40. Components (a+b) and (c) may be contained in a ratio by weight of 0.01:99.9 to 2:98, preferably 0.5:99.5 to 1.5:98.5, and particularly preferably about 1:99. The total content of components (a+b) in the final products may be between 1 and 5,000, preferably 10 to 4,000, and particularly preferably 100 to 1,000 ppm.

The cosmetic and/or pharmaceutical substances may also contain typical auxiliaries and additives, such as e.g. mild surfactants, oil components, emulsifiers, pearlescent waxes, consistency-enhancing agents, thickeners, superfatting agents, stabilizers, polymers, silicone compounds, fats, waxes, lecithins, phospholipids, UV light protection factors, humectants, biogenic agents, antioxidants, deodorants, antiperspirants, antidandruff agents, film-forming agents, swelling agents, insect repellents, self-tanning agents, tyrosine inhibitors (depigmentation agents), hydrotropes, solubilizers, preservatives, perfume oils, dyes and the like.

Surfactants

The compositions may contain surface-active substances such as anionic, nonionic, cationic and/or amphoteric or zwitterionic surfactants, whose content ordinarily averages about 1 to 70, preferably 5 to 50, and particularly preferably 10 to 30 wt %. Typical examples of anionic surfactants are soaps, alkylbenzene sulfonates, alkane sulfonates, olefin sulfonates, alkyl ether sulfonates, glycerol ether sulfonates, $\alpha$-methylester sulfonates, sulfofatty acids, alkyl sulfates, alkyl ether sulfates, glycerol ether sulfates, fatty acid ether sulfates, hydroxy mixed ether sulfates, monoglyceride (ether)sulfates, fatty acid amide(ether)sulfates, mono- and dialkylsulfosuccinates, mono- and dialkylsulfosuccinamates, sulfotriglycerides, amide soaps, ether carboxylic acids and salts thereof, fatty acid isethionates, fatty acid sarcosinates, fatty acid taurides, N-acylamino acids, such as e.g. acyl lactylate, acyl tartrate, acyl glutamate, and acyl aspartate, alkyloligoglucoside sulfates, protein fatty acid condensates (particularly wheat-based plant products) and alkyl(ether)phosphates. If the anionic surfactants contain polyglycol ether chains, these may show a conventional, but preferably narrowed homologous distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yloligoglycosides or glucuronic acid derivatives, fatty acid N-alkyl glucamides, protein hydrolysates (particularly wheat-based plant products), polyol fatty acid esters, sugar esters, sorbitan esters, polysorbates, and amine oxides. If the nonionic surfactants contain polyglycol ether chains, these may show a conventional, but preferably narrowed homologous distribution. Typical examples of cationic surfactants are quaternary ammonium compounds, such as e.g. dimethyl distearylammonium chloride and esterquats, particularly quaternized fatty acid trialkanolamine ester salts. Typical examples of amphoteric or zwitterionic surfactants are alkyl betaine, alkylamidobetaine, aminopropionate, aminoglycinate, imidazolinium betaine and sulfobetaine. All of the aforementioned surfactants are known compounds. Typical examples of particularly suitable mild, i.e. particularly skin-compatible surfactants, are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, $\alpha$-olefinsulfonates, ether carboxylic acids, alkyl oligoglucosides, fatty acid glucamides, alkylamidobetaine, amphoacetals, and/or protein fatty acid condensates, the latter preferably based on wheat proteins.

Oil Components

Suitable examples of oil components include Guerbet alcohols based on fatty alcohols with 6 to 18, and preferably 8 to 10 carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate, and erucyl erucate. Other suitable substances include esters of linear $C_6$-$C_{22}$ fatty acids with branched alcohols, particularly 2-ethylhexanol, esters of $C_{18}$-$C_{36}$ alkylhydroxycarboxylic acids with linear or branched $C_6$-$C_{22}$ fatty alcohols, particularly dioctyl malate, esters of linear and/or branched fatty acids with polyhydric alcohols (such as e.g. propylene glycol, dimer diol or trimer triol) and/or Guerbet alcohols, triglycerides based on $C_6$-$C_{10}$ fatty acids, liquid mono/di/triglyceride mixtures based on $C_6$-$C_{18}$ fatty acids, esters of $C_6$-$C_{22}$ fatty alcohols and/or Guerbet alcohols with aromatic carboxylic acids, particularly benzoic acid, esters of $C_2$-$C_{12}$ dicarboxylic acids with linear or branched alcohols with 1 to 22 carbon atoms or polyols with 2 to 10 carbon atoms and 2 to 6 hydroxyl groups, vegetable oils, branched primary alcohols, substituted cyclohexanes, linear and branched $C_6$-$C_{22}$ fatty alcohol carbonates, such as e.g. dicaprylyl carbonate (Cetiol® CC), Guerbet carbonates based on fatty alcohols with 6 to 18, and preferably 8 to 10 C atoms, esters of benzoic acid with linear and/or branched $C_6$-$C_{22}$ alcohols (e.g. Finsolv® TN), linear or branched, symmetrical or unsymmetrical dialkyl ethers with 6 to 22 carbon atoms per alkyl group, such as e.g. dicaprylyl ether (Cetiol® OE), ring-opening products of epoxidized fatty acid esters with polyols, silicone oils (cyclomethicones, silicon methicone products, etc.) and/or aliphatic or naphthenic hydrocarbons, such as e.g. squalane, squalene, or dialkyl cyclohexanes.

Emulsifiers

Examples of suitable emulsifiers include nonionogenic surfactants from at least one of the following groups:
  addition products of 2 to 30 mol of ethylene oxide and/or 0 to 5 mol of propylene oxide to linear fatty alcohols with 8 to 22 C atoms, fatty acids with 12 to 22 C atoms, alkylphenols with 8 to 15 C atoms in the alkyl group, and alkylamines with 8 to 22 carbon atoms in the alkyl residue;
  alkyl and/or alkenyl oligoglycosides with 8 to 22 carbon atoms in the alk(en)yl residue and ethoxylated analogs thereof;
  addition products of 1 to 15 mol of ethylene oxide to castor oil and/or hydrogenated castor oil;
  addition products of 15 to 60 mol of ethylene oxide to castor oil and/or hydrogenated castor oil;
  partial esters of glycerol and/or sorbitan with unsaturated, linear or saturated, branched fatty acids with 12 to 22 carbon atoms and/or hydroxycarboxylic acids with 3 to 18 carbon atoms, as well as adducts thereof with 1 to 30 mol of ethylene oxide;
  partial esters of polyglycerol (average degree of self-condensation of 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside), as well as polyglucosides (e.g. cellulose) with saturated and/or unsaturated, linear or branched fatty acids with 12 to 22 carbon atoms and/or hydroxycarboxylic acids with 3 to 18 carbon atoms, as well as adducts thereof with 1 to 30 mol of ethylene oxide;
  mixed esters of pentaerythritol, fatty acids, citric acid, and fatty alcohols and/or mixed esters of fatty acids with 6 to 22 carbon atoms, methylglucose and polyols, preferably glycerol or polyglycerol.
  mono-, di- and trialkylphosphates, as well as mono-, di- and/or tri-PEG alkyl phosphates and salts thereof;
  lanolin alcohols;
  polysiloxane-polyalkyl-polyether copolymers or corresponding derivatives;
  block copolymers, e.g. polyethylene glycol-30 dipolyhydroxystearates;
  polymer emulsifiers, e.g. Pemulen types (TR-1,TR-2) from Goodrich or Cosmedia® SP from Cognis;
  polyalkylene glycols, as well as
  glycerol carbonate.

In the following, particularly suitable emulsifiers are explained in further detail:

(a) Alkoxylates

The addition products of ethylene oxide and/or propylene oxide to fatty alcohols, fatty acids, alkylphenols or castor oil constitute known, commercially available products. These are homologous mixtures whose average degree of alkoxylation corresponds to the ratio of the amounts of ethylene oxide and/or propylene oxide and the substrate with which the addition reaction is carried out. $C_{12/18}$ fatty acid mono- and diesters of addition products of ethylene oxide to glycerol are known as refatting agents for cosmetic preparations.

(a) Alkyl and/or Alkenyloligoglycosides

Alkyl and/or alkenyloligoglycosides, their manufacture, and their application are known from the prior art. Their manufacture is carried out in particular by the reaction of glucose or oligosaccharides with primary alcohols with 8 to 18 carbon atoms. With respect to the glycoside residue, both monoglycosides, in which a cyclical sugar residue is glycosidically bonded to the fatty alcohol, and oligomeric glycosides, preferably with a degree of oligomerization of up to about 8, are suitable. Here, the degree of oligomerization is a statistical average value that is based on a homologous distribution that is common for such technical products.

(b) Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric diglyceride, malic acid monoglyceride, malic acid diglyceride, as well as technical mixtures thereof, which may also contain small amounts of triglyceride secondarily produced in the manufacturing process. Also suitable are addition products of 1 to 30, and preferably 5 to 10 mol of ethylene oxide to the above-mentioned partial glycerides.

(c) Sorbitan Esters

Examples of suitable sorbitan esters include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricin oleate, sorbitan sesquiricin oleate, sorbitan diricin oleate, sorbitan triricin oleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, as well as technical mixtures thereof. Also suitable are addition products of 1 to 30, and preferably 5 to 10 mol of ethylene oxide to the above-mentioned sorbitan esters.

(d) Polyglycerol Esters

Typical examples of suitable polyglycerol esters are polyglyceryl-2 dipolyhydroxystearate (Dehymuls® PGPH), polyglycerol-3-diisostea rate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32), and polyglyceryl polyricin oleate (Admul® WOL 1403), polyglyceryl dimerate isostearate, as well as mixtures thereof. Examples of other suitable polyol esters are mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

(e) Anionic Emulsifiers

Typical anionic emulsifiers are aliphatic fatty acids with 12 to 22 carbon atoms, such as e.g. palmitic acid, stearic acid or behenic acid, as well as dicarboxylic acids with 12 to 22 carbon atoms, such as e.g. azelaic acid or sebacic acid.

(f) Amphoteric and Cationic Emulsifiers

Zwitterionic surfactants may also be used as emulsifiers. The term zwitterionic surfactants refers to surface-active compounds having at least one quaternary ammonium group and at least one carboxylate and one sulfonate group in the molecule. Particularly suitable zwitterionic surfactants are those referred to as betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxylmethyl-3-hydroxyethylimidazolines having 8 to 18 C atoms in the alkyl or acyl group respectively, as well as cocoacylaminoethylhydroxyethylcarboxymethyl glycinate. Particularly preferred is the fatty acid amide derivative known by the CTFA name Cocamidopropyl Betaine. Ampholytic surfactants are also suitable emulsifiers. The term ampholytic surfactants is understood to refer to those surface-active compounds which contain at least one free amino group and at least one —COOH or —SO$_3$H group in the molecule in addition to a C$_{8/18}$ alkyl or acyl group, and are capable of forming internal salts. Examples of suitable ampholytic surfactants are N-alkylglycine, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids with about 8 to 18 C atoms in the alkyl group respectively. Particularly preferred ampholytic surfactants are N-cocoalkyl aminopropionate, cocoacylaminoethyl aminopropionate, and C$_{12/18}$ acylsarcosine. Finally, cationic surfactants are also suitable as emulsifiers, with those of the esterquat type, preferably methylquaternized difatty acid triethanolamin ester salts, being particularly preferred.

Fats and Waxes

Typical examples of fats are glycerides, i.e. solid or liquid plant or animal products, which are essentially composed of mixed glycerol esters of higher fatty acids, suitable waxes include, for example, natural waxes, such as e.g. candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (woolwax), uropygial fat, ceresin, ozokerite (earth wax), petrolatum, paraffin waxes, microwaxes; chemically modified waxes (hard waxes), such as e.g. montan ester waxes, sasol waxes, hydrogenated jojoba waxes such as synthetic waxes, e.g. polyalkylene waxes and polyethylene glycol waxes. In addition to fats, fat-like substances are also suitable as additives, such as lecithins and phospholipids. The term lecithins is understood by the person having ordinary skill in the art as referring to glycerophospholipids which are formed by esterification from fatty acids, glycerol, phosphoric acid, and choline. Therefore, lecithins are often also referred to in the expert community as phosphatidylcholines (PC). Examples of natural lecithins include the cephalins which are also referred to as phosphatidic and constitute derivatives of 1,2-diacyl-sn-glycerol-3-phosphoric acids. In contrast, phospholipids are usually understood to refer to mono- and preferably diesters of phosphoric acid with glycerol (glycerol phosphate), which are generally classified as fats. Sphingosines or sphingolipids are also suitable.

Pearlescent Waxes

Examples of pearlescent waxes include: alkylene glycol esters, particularly ethylene glycol distearate; fatty acid alkanolamides, particularly coconut fatty acid diethanolamide; partial glycerides, particularly stearic acid monoglyceride; esters of polyvalent, optionally hydroxy-substituted carboxylic acids with fatty alcohols having 6 to 22 carbon atoms, particularly long-chain esters of tartaric acid; fatty substances, such as e.g. fatty alcohols, fatty ketones, fatty aldehydes, fatty ethers, and fatty carbonates, which have a total of at least 24 carbon atoms, particularly laurone and distearyl ether; fatty acids such as stearic acid, hydroxystearic acid or behenic acid, ring-opening products of olefin epoxides having 12 to 22 carbon atoms with fatty alcohols with 12 to 22 carbon atoms and/or polyols having 2 to 15 carbon atoms and 2 to 10 hydroxyl groups, and mixtures thereof.

Consistency-Enhancing Agents and Thickeners

Primarily suitable as consistency-enhancing agents are fatty alcohols or hydroxy fatty alcohols with 12 to 22 and preferably 16 to 18 carbon atoms, and partial glycerides, fatty acids, or hydroxy fatty acids are also suitable. Preferred is a combination of these substances with alkyl oligoglucosides and/or fatty acid-N-methyl glucamides of the same chain length and/or polyglycerol poly-12-hydroxystearates. Suitable thickeners are for example aerosils (hydrophilic silicic acids), polysaccharides, particularly xanthan gum, guar-guar, agar-agar, alginates and tyloses, carboxymethyl cellulose and hydroxyethyl and hydroxypropyl cellulose, as well as higher-molecular-weight polyethylene glycol mono- and diesters of fatty acids, polyacrylates, (e.g. the Carbopole® and Pemulen product lines from Goodrich; Synthalene® from Sigma; the Keltrol product line from Kelco; the Sepigel product line from Seppic; the Salcare product line from Allied Colloids), polyacrylamides, polymers, polyvinyl alcohol and polyvinylpyrrolidone. Bentonites, such as e.g. Bentone® Gel VS-SPC (Rheox), which are a mixture of cyclopentasiloxane, disteardimonium hectorite, and propylene carbonate, have also been found to be particularly effective. Also suitable are surfactants, such as e.g. ethoxylated fatty acid glycerides, esters of fatty acids with polyols such as e.g. pentaerythritol or trimethylolpropane, fatty alcohol ethoxylates with a narrowed homologous distribution, or alkyl oligoglucosides, as well as electrolytes such as sodium chloride and ammonium chloride.

Superfatting Agents

Superfatting agents suitable for use are substances such as e.g. lanolin and lecithin, as well as polyethoxylated or acylated lanolin and lecithin derivatives, polyol fatty acid esters, monoglycerides, and fatty acid alkanolamides, wherein the latter also serve as foam stabilizers.

Stabilizers

As stabilizers, metal salts of fatty acids, such as e.g. magnesium, aluminum, and/or zinc stearate or ricinoleate, may be used.

Polymers

Suitable cationic polymers are for example cationic cellulose derivatives, such as e.g. a quaternized hydroxyethyl cellulose available from Amerchol under the name JR 400®, cationic starch, copolymers of diallylammonium salts and acrylamides, quaternized vinylpyrrolidone/vinylimidazole polymers, such as e.g. Luviquat® (BASF), condensation products of polyglycols and amines, quaternized collagen polypeptides, such as e.g. lauryldimonium hydroxypropyl hydrolyzed collagen (Lamequat® L/Grunau), quaternized wheat polypeptides, polyethylenimine, cationic silicone polymers, such as e.g. amodimethicone, copolymers of adipic acid and dimethylaminohydroxypropyldiethylenetriamine (Cartaretine®/Sandoz), copolymers of acrylic acid with dimethyl diallylammonium chloride (Merquat® 550/Chemviron), polyaminopolyamides and crosslinked water-soluble polymers thereof, cationic chitin derivatives such as e.g. quaternized chitosan, optionally in the form of a microcrystalline dispersion, condensation products of dihalogenalkylenes such as e.g. dibromobutane with bis-dialkylamines such as e.g. bis-dimethylamino-1,3-propane, cationic guar gum, such as e.g. Jaguar® CBS, Jaguar® C-17, or Jaguar® C-16 from Celanese, quaternized ammonium salt polymers, such as e.g. Mirapol® A-15, Mirapol® AD-1, Mirapol® AZ-1 from Miranol.

Examples of suitable anionic, zwitterionic, amphoteric, and nonionic polymers include vinyl acetate/crotonic acid copolymers, vinylpyrrolidone/vinylacrylate copolymers, vinyl acetate/butyl maleate/isobornyl acrylate copolymers, methylvinyl ether/maleic anhydride copolymers and esters thereof, uncrosslinked polyacrylic acids and those cross-linked with polyols, acrylamidopropyltrimethylammonium chloride/acrylate copolymers, octylacrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers, as well as optionally derivatized cellulose ether and silicones.

Silicone Compounds

Suitable silicone compounds are for example dimethyl polysiloxanes, methylphenyl polysiloxanes, cyclic silicones, as well as amino, fatty-acid, alcohol, polyether, epoxy, fluorine, glycoside and/or alkyl-modified silicone compounds, which may be either liquid or resinous at room temperature. Also suitable are simethicones, which are mixtures of dimethicones with an average chain length of 200 to 300 dimethyl siloxane units, and hydrogenated silicates.

UV Light Protection Factors

The term UV light protection factors is understood, for example to refer to organic substances that are liquid or crystalline at room temperature (light protection filters), which are capable of absorbing ultraviolet radiation and then giving off the absorbed energy in the form of longer-wavelength radiation, e.g. heat. Ordinarily, the UV light protection factors are present in amounts of 0.1 to 5, and preferably 0.2 to 1 wt %. UVB filters may be oil-soluble or water-soluble. The following can be mentioned as examples of oil-soluble substances, e.g.:

3-benzylidene camphor or 3-benzylidene norcamphor and derivatives thereof, e.g. 3-(4-methylbenzylidene)camphor;

4-aminobenzoic acid derivatives, preferably 4-(dimethylamino)benzoic acid-2-ethylhexyl ester, 4-(dimethylamino)benzoic acid-2-octyl ester, and 4-(dimethylamino) benzoic acid amyl ester;

esters of cinnamic acid, preferably 4-methoxycinnamic acid-2-ethylhexyl ester, 4-methoxy-cinnamic acid propyl ester, 4-methoxycinnamic acid isoamyl ester, and 2-cyano-3,3-phenylcinnamic acid-2-ethylhexyl ester (octocrylene);

esters of salicylic acid, preferably salicylic acid-2-ethylhexyl ester, salicylic acid-4-iso-propylbenzyl ester, and salicylic acid homomenthyl ester;

Benzophenone derivatives, preferably 2-hydroxy-4-methoxybenzophenone, 2-hydroxy-4-methoxy-4'-methylbenzophenone, and 2,2'-dihydroxy-4-methoxybenzophenone;

esters of benzalmalonic acid, preferably 4-methoxybenzalmalonic acid di-2-ethylhexyl ester;

Triazine derivatives, such as e.g. 2,4,6-trianilino-(p-carbo-2'-ethyl-1'-hexyloxy)-1,3,5-triazine and octyltriazone or dioctylbutamidotriazone (Uvasorb® HEB);

Propane-1,3-diones such as e.g. 1-(4-tert-butylphenyl)-3-(4'-methoxyphenyl)propane-1,3-dione;

Ketotricyclo(5.2.1.0)decane derivatives.

Suitable water-soluble substances include:

2-phenylbenzimidazole-5-sulfonic acid and alkali, alkaline earth, ammonium, alkylammonium, alkanolammonium, and glucammonium salts thereof;

1H-benzimidazole-4,6-disulfonic acid, 2,2'-(1,4-phenylene) bis-disodium salt (Neo Heliopan® AP)

Sulfonic acid derivatives of benzophenones, preferably 2-hydroxy-4-methoxybenzophenone-5-sulfonic acid and salts thereof;

Sulfonic acid derivatives of 3-benzylidene camphor, such as e.g. 4-(2-oxo-3-bornylidene methyl)benzenesulfonic acid and 2-methyl-5-(2-oxo-3-bornylidene)sulfonic acid and salts thereof.

Among typical UV-A filters, derivatives of benzoylmethane are particularly suitable, such as e.g. 1-(4'-tert-butylphenyl)-3-(4'-methoxyphenyl)propane-1,3-dione, 4-tert-butyl-4'-methoxydibenzoylmethane (Parsol® 1789), 2-(4-diethylamino-2-hydroxybenzoyl)-benzoic acid hexyl ester (Uvinul® A Plus), 1-phenyl-3-(4'-isopropylphenyl)-propane-1,3-dione, as well as enamine compounds. The UV-A and UV-B filters may of course also be used in mixtures. Particularly favorable combinations consist of derivatives of benzoylmethane, e.g. 4-tert-butyl-4'-methoxydibenzoyl-methane (Parsol® 1789) and 2-cyano-3,3-phenylcinnamic acid-2-ethyl-hexyl ester (octocrylene) in combination with esters of cinnamic acid, preferably 4-methoxycinnamic acid-2-ethylhexyl ester and/or 4-methoxycinnamic acid propyl ester and/or 4-methoxycinnamic acid isoamyl ester. Advantageously, such combinations are combined with water-soluble filters such as e.g. 2-phenylbenzimidazole-5-sulfonic acid and alkali, alkaline earth, ammonium, alkylammonium, alkanolammonium, and glucammonium salts thereof.

In addition to the above-mentioned soluble substances, insoluble light protection pigments are also suitable for this purpose, i.e. finely-dispersed metal oxides or salts. Examples of particularly suitable metal oxides are zinc oxide and titanium dioxide, oxides of iron, zirconium, silicon, manganese, aluminum and cerium, as well as mixtures thereof. Silicate (talc), barium sulfate, or zinc stearate may be used as salts. The oxides and salts are used in the form of pigments for in the form of skin care skin care and skin protective emulsions and decorative cosmetics. In this case, the particles have an average diameter of less than 100 nm, preferably between 5 and 50 nm, and particularly preferably between 15 and 30 nm. They may have a spherical shape, but particles may also be used that have an ellipsoid shape or deviate from spherical form in any other manner. The pigments may also be surface-treated, i.e. be in hydrophilized or hydrophobized. Typical examples are coated titanium dioxides, such as e.g. titanium dioxide T 805 (Degussa) or Eusolex® T2000, Eusolex® T, Eusolex® T-ECO, Eusolex® T-S, Eusolex® T-Aqua, Eusolex® T-45D (all Merck), Uvinul $TiO_2$ (BASF). As hydrophobic coating agents, silicones are preferred, and trialkoxyoctylsilanes or simethicones are particularly preferred. In sunscreen products, substances referred to as micro- or nanopigments are preferably used. Micronized zinc oxides such as e.g. Z-COTE® or Z-COTE HP1® are most preferably used.

Humectants

Humectants are used for further optimization of the sensory properties of the composition and for moisture regulation of the skin. At the same time, the cold stability of the preparations according to the invention, particularly in the case of emulsions, is increased. Humectants are ordinarily contained in an amount of 0.1 to 15 wt %, preferably 1 to 10 wt %, and particularly preferably 5 to 10 wt %.

Examples of suitable substances according to the invention are amino acids, pyrrolidone carboxylic acid, lactic acid and salts thereof, lactitol, urea and urea derivatives, uric acid, glucosamine, creatinine, collagen cleavage products, chitosan or chitosan salts/derivatives, and particularly polyols and polyol derivatives (e.g. glycerol, diglycerol, triglycerol, ethylene glycol, propylene glycol, butylene glycol, erythritol, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20), sugars and sugar derivatives (including fructose, glucose, maltose, maltitol, mannitol, inositol, sorbitol, sorbityl silanediol, sucrose, trehalose, xylose, xylitol, glucuronic acid, and salts thereof), ethoxylated sorbitol (Sorbeth-6, Sorbeth-20, Sorbeth-30, Sorbeth-40), honey and hydrogenated honey, hydrogenated starch hydrolysate, as well as mixtures of hydrogenated wheat protein and PEG-20-acetate copolymer. Preferred according to the invention as humectants are glycerol, diglycerol, triglycerol, and butylene glycol.

Biogenic Agents and Antioxidants

Biogenic agents are understood to refer, for example, to tocopherol, tocopherol acetate, tocopherol palmitate, ascorbic acid, (deoxy)ribonucleic acid and fragmentation products thereof, β-glucane, retinol, bisabolol, allantoin, phytantriol, panthenol, AHA acids, amino acids, ceramides, pseudoceramides, essential oils, plant extracts, such as e.g. prunus extract, bambara nut extract, and vitamin complexes.

Antioxidants disrupt the photochemical reaction chain that is triggered when UV radiation penetrates the skin. Typical examples of these substances are amino acids (e.g. glycine, histidine, tyrosine, tryptophan) and derivatives thereof, imidazole (e.g. urocanic acid) and derivatives thereof, peptides such as D,L-carnosine, D-carnosine, L-carnosine and derivatives thereof (e.g. anserine), carotinoids, carotenes (e.g. α-carotene, β-carotene, lycopene) and derivatives thereof, chlorogenic acid and derivatives thereof, liponic acid and derivatives thereof (e.g. dihydroliponic acid), aurothioglucose, propylthiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) as well as salts thereof, dilauryl thiodipropionate, distearyl thiodipropionate, thiodipropionic acid and derivatives thereof (esters, ethers, peptides, lipids, nucleotides, nucleosides and salts), as well as sulfoximine compounds (e.g. buthionine sulfoximine, homocysteine sulfoximine, buthioninsulfone, penta-, hexa-, heptathioninsulfoximine) in very low tolerable dosages (e.g. pmol to µmol/kg), further (metal) chelators (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), as well as coniferyl benzoate from benzoin, rutic acid and derivatives thereof, α-glycosylrutin, ferulic acid, furfurylidene glucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenium methionine), stilbenes and derivatives thereof (e.g. stilbene oxide, trans-stilbene oxide) and suitable derivatives according to the invention of the above-mentioned active ingredients (salts, esters, ethers, sugars, nucleotides, nucleosides, peptides and lipids).

Deodorants and Antibacterial Agents

Cosmetic deodorants (deodorizing agents) counteract, mask, or eliminate body odors. Body odors occur due to the effect of skin bacteria on apocrine perspiration, causing the formation of unpleasant-smelling degradation product. Accordingly, deodorants contain active ingredients that function as bacteriostatic agents, enzyme inhibitors, odor absorbers, or odor-masking agents.

(a) Bacteriostatic Agents

Suitable bacteriostatic agents are generally all substances active against gram-positive bacteria, such as e.g. 4-hydroxybenzoic acid and salts and esters thereof, N-(4-chlorophenyl)-N'-(3,4-dichlorophenyl)urea, 2,4,4'-trichloro-2'-hydroxy-diphenylether (triclosan), 4-chloro-3,5-dimethylphenol, 2,2'-methylene-bis(6-bromo-4-chlorophenol), 3-methyl-4-(1-methylethyl) phenol, 2-benzyl-4-chlorophenol, 3-(4-chlorophenoxy)-1,2-propanediol, 3-iodo-2-propinylbutylcarbamate, chlorhexidine, 3,4,4'-trichlorocarbanilide (TTC), antibacterial fragrances, thymol, thyme oil, eugenol, clove oil, menthol, mint oil, farnesol, phenoxyethanol, glycerol monocaprinate, glycerol monocaprylate, glycerol monolaurate (GML), diglycerol monocaprinate (DMC), and salicylic acid-N-alkylamides such as e.g. salicylic acid-n-octylamide or salicylic acid-n-decylamide.

(b) Enzyme Inhibitors

Esterase inhibitors, for example, are suitable enzyme inhibitors. These are preferably trialkyl citrates such as trimethyl citrate, tripropyl citrate, triisopropyl citrate, and tributyl citrate, and particularly preferably triethyl citrate (Hydagen® CAT). These substances inhibit enzyme activity and thus reduce odor formation. Further substances that are suitable as esterase inhibitors are sterol sulfates or phosphates, such as e.g. lanosterol, cholesterol, campesterol, stigmasteron, and sitosterol sulfate or phosphate, dicarboxylic acids and esters thereof such as e.g. glutaric acid, glutaric acid monoethyl esters, glutaric acid diethyl esters, adipic acid, adipic acid monoethyl esters, adipic acid diethyl esters, malonic acid and malonic acid diethyl esters, hydroxycarboxylic acids and esters thereof such as e.g. citric acid, malic acid, tartaric acid or tartaric acid diethyl esters, as well as zinc glycinate.

(c) Odor Absorbers

Suitable odor absorbers are substances that are able to absorb odor-forming compounds and largely retain them. They reduce the partial pressure of the individual components and this also reduces their rate of diffusion. In this case, it is important that perfumes must remain unaffected. Odor absorbers have no efficacy against bacteria. They contain, for example, as the main component a complex zinc salt of ricinoleic acid or special, largely odor-neutral fragrances, which are known to the person having ordinary skill in the art as "fixators", such as e.g. extracts of labdanum or styrax or certain abietic acid derivatives. Odor-masking agents function are fragrances or perfume oils, which in addition to their function as odor-masking agents provide deodorants with their respective scents. Examples of perfume oils include, for example, mixtures of natural and synthetic fragrances. Natural fragrances are extracts of flowers, stems and leaves, fruits, fruit peels, roots, woods, herbs and grasses, needles and branches, as well as resins and balsams. Also suitable are animal raw materials, such as e.g. civet and castoreum. Typical synthetic fragrance compounds are products of the type of the esters, ethers, aldehydes, ketones, alcohols, and hydrocarbons. Fragrance compounds of the ester type are e.g. benzyl acetate, p-tert-butylcyclohexyl acetate, linalyl acetate, phenylethyl acetate, linalyl benzoate, benzyl formiate, allylcyclohexyl propionate, styrallyl propionate and benzyl salicylate. Examples of ethers include benzylethyl ether, and examples of aldehydes include linear alkanals with 8 to 18 carbon atoms, citral, citronellal, citronellyl oxyacetaldehyde, cyclamen aldehyde, hydroxycitronellal, lilial and bourgeonal, examples of ketones are the ionones and methyl cedryl ketone, examples of the alcohols are anethole, citronellol, eugenol, isoeugenol, geraniol, linalool, phenylethyl alcohol and terpineol, and examples of the hydrocarbons are mainly the terpenes and balsams. Preferred, however, is the use of mixtures of different fragrances, which together produce a pleasant scent. Ethereal oils of low volatility, which are usually used as aroma components, are suitable as perfume oils, e.g. sage oil, camomile oil, clove oil, melissa oil, mint oil, cinnamon leaf oil, linden flower oil, juniper berry oil, vetiver oil, olibanum oil, galbanum oil, labdanum oil, and lavandin oil. Preferably, bergamot oil, dihydromyrcenol, lilial, lyral, citronellol, phenyl ethyl alcohol, α-hexyl cinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat are used, individually or in mixtures.

(d) Antiperspirants

Antiperspirants (antiperspirant agents) reduce the formation of perspiration by affecting the activity of the eccrine sweat glands, thus counteracting underarm wetness and body odor. Aqueous or anhydrous formulations of antiperspirants typically comprise the following ingredients:

astringent agents, oil components, nonionic emulsifiers, coemulsifiers, consistency-enhancing agents, excipients such as e.g. thickeners or complexing agents and/or nonaqueous solvents such as e.g. ethanol, propylene glycol and/or glycerol.

Suitable as astringent antiperspirant agents are primarily salts of aluminum, zirconium, or zinc. Examples of such suitable antihydrotically active agents are aluminum chloride, aluminum chlorohydrate, aluminum dichlorohydrate, aluminum sesquichlorohydrate, and complex compounds thereof, e.g. with propylene glycol-1,2-aluminum hydroxyallantoinate, aluminum chloride tartrate, aluminum zirconium trichlorohydrate, aluminum zircon tetrachlorohydrate, aluminum zircon pentachlorohydrate and complex compounds thereof, e.g. with amino acids such as glycine. In addition, antiperspirants may also contain common oil-soluble and water-soluble auxiliaries in small amounts. Examples of such oil-soluble auxiliaries may be:

antiinflammatory, skin protective, or fragrant ethereal oils, synthetic skin protective agents and/or oil-soluble perfume oils.

Common water-soluble additives are e.g. preservatives, water-soluble fragrances, pH adjusters, e.g. buffer mixtures, water-soluble thickeners, e.g. water-soluble natural or synthetic polymers such as e.g. xanthan gum, hydroxyethyl cellulose, polyvinylpyrrolidone or high molecular weight polyethylene oxides.

Film-Forming Agents

Common film-forming agents are for example chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid, or salts thereof and similar compounds.

Antidandruff Agents

Suitable antidandruff agents include piroctone olamine (1-hydroxy-4-methyl-6-(2,4,4-trimethylpentyl)-2-(1H)-pyridinone monoethanolamine salt), Baypival® (climbazole), Ketoconazol®, (4-acetyl-1-{-4-[2-(2,4-dichlorophenyl) r-2-(1H-imidazole-1-ylmethyl)-1,3-dioxylane-c-4-ylmethoxyphenyl}piperazine, ketoconazole, elubiol, selenium disulfide, colloidal sulfur, sulfur polyethylene glycol sorbitan monooleate, sulfur rizinol polyethoxylate, sulfur-tar distillates, salicylic acid (or in combination with hexachlorophene), undecylenic acid monoethanolamide sulfosuccinate Na-salt, Lamepon® UD (protein-undecylenic acid condensate), zinc pyrithione, aluminum pyrithione, and magnesium pyrithione/dipyrithione-magnesium sulfate.

Swelling Agents

Swelling agents for aqueous phases may be montmorillonites, clay mineral substances, Pemulen, as well as alkyl-modified carbopols (Goodrich). Further suitable polymers or swelling agents may be seen in the overview of R. Lochhead in Cosm. Toil. 108, 95 (1993).

Insect Repellents

Suitable insect repellents are N,N-diethyl-m-toluamide, 1,2-pentanediol, or ethyl butylacetylaminopropionate. Dihydroxyacetone is suitable as a self-tanning agent. Examples of suitable tyrosine inhibitors, which prevent the formation of melanin and are used in depigmentation agents, include arbutin, ferulic acid, kojic acid, cumaric acid and ascorbic acid (vitamin C).

Ingredients for Oral and Dental Core Products

Arbutin toothpastes or tooth creams are generally understood to refer to gel-type or pasty preparations of water, thickeners, humectants, polishing or abrasive particles, surfactants, sweeteners, aromatic substances, deodorizing agents, as well as agents against oral and dental diseases. In the toothpastes according to the invention, all common abrasive particles, such as e.g. chalk, dicalcium phosphate, insoluble sodium metaphosphate, aluminum silicates, calcium pyrophosphate, fine particle artificial resins, silicic acids, aluminum oxide, and aluminum oxide trihydrate may be used.

Preferred suitable abrasive particles for the toothpastes according to the invention are chiefly fine particle xerogel silicic acids, hydrogel silicic acids, precipitated silicic acids, aluminum oxide trihydrate, and fine particle alpha-aluminum oxide or mixtures of these abrasive particles in amounts of 15 to 40 wt % of the toothpaste. Suitable as humectants are primarily low molecular weight polyethylene glycols, glycerol, sorbitol or mixtures of these products in amounts of up to 50 wt %. Among the known thickeners, the thickening, fine particle gel silicic acids and hydrocolloids, such as e.g. carboxymethyl cellulose, hydroxyethyl cellulose, hydroxypropyl guar, hydroxyethyl starch, polyvinylpyrrolidone, high-molecular weight polyethylene glycol, plant gums such as traganth, agar-agar, carrageen moss, gum arabic, xanthan gum, and carboxyvinyl polymers (e.g. Carbopol® products) are suitable. In addition to the mixtures of menthofuran and menthol compounds, the oral and dental care products may contain in particular surface-active substances, preferably anionic and nonionic high-foaming surfactants, such as the above-mentioned substances, particularly, however, alkyl ether sulfate salts, alkyl polyglucosides, and mixtures thereof.

Further common toothpaste additives are:
preservatives and antimicrobial substances such as e.g. p-hydroxybenzoic acid methyl, ethyl or propyl esters, sodium sorbate, sodium benzoate, bromochlorophene, phenylsalicylic acid esters, thymol and the like;
anti-tartar agents, e.g. organophosphates such as 1-hydroxyethane-1.1-diphosphonic acid, 1-phosphonopropane-1,2,3-tricarboxylic acid and others which are known e.g. from U.S. Pat. No. 3,488,419, DE 2224430 A1 and DE 2343196 A1;
other cavity-preventing substances such as e.g. sodium fluoride, sodium monofluorophosphate, stannous fluoride;
sweeteners such as e.g. sodium saccharin, sodium cyclamate, sucrose, lactose, maltose, fructose or Aspartame®, (L-aspartyl-L-phenylalanine methyl ester), stevia extracts, or sweetening components thereof, particularly ribaudioside;
additional aromatic agents such as e.g. eucalyptus oil, aniseed oil, fennel oil, caraway seed oil, methyl acetate, cinnamic aldehyde, anethol, vanillin, thymol, as well as mixtures of these and other natural and synthetic aromatic agents;
pigments such as e.g. titanium dioxide;
dyes;
buffer substances such as e.g. primary, secondary or tertiary alkali phosphates, or citric acid/sodium citrate;
wound-healing and antiinflammatory substances such as e.g. allantoin, urea, azulene, camomile active ingredients and acetylsalicylic acid derivatives.

In a preferred embodiment of the cosmetic preparations, toothpastes are in the form of an aqueous, pasty dispersion containing polishing agents, humectants, viscosity regulators, and optionally other common components, as well as a mixture of menthofuran and menthol compounds in amounts of 0.5 to 2 wt %.

In mouthwashes, a combination with aqueous alcohol solutions containing various concentrations of ethereal oils, emulsifiers, astringents, and tonifying medicinal extracts, anti-tartar, antibacterial additives and flavor adjusters is quite possible. Another preferred embodiment of the invention is a mouthwash in the form of an aqueous or aqueous alcohol solution containing a mixture of menthofuran and menthol compounds in amounts of 0.5 to 2 wt %. In mouthwashes that are diluted before use, sufficient effects can be achieved with higher concentrations, depending on the dilution ratio in question.

Hydrotropes

In addition, in order to improve flow behavior, hydrotropes, such as e.g. ethanol, isopropyl alcohol, or polyols may be used; these substances largely correspond to the carriers described at the outset. Polyols that are suitable for this purpose should preferably have 2 to 15 carbon atoms and at least two hydroxyl groups. The polyols may also contain other functional groups, particularly amino groups, or be modified with nitrogen. Typical examples are:
glycerol;
alkylene glycols, such as e.g. ethylene glycol, diethylene glycol, propylene glycol, butylene glycol, hexylene glycol, as well as polyethylene glycols with an average molecular weight of 100 to 1,000 daltons;
technical oligoglycerol mixtures with a degree of self-condensation of 1.5 to 10 such as, for example, technical diglycerol mixtures with a diglycerol content of 40 to 50 wt %;
methyol compounds, such as particularly trimethylol ethane, trimethylol propane, trimethylol butane, pentaerythritol and dipentaerythritol;
lower alkyl glucosides, particularly those with 1 to 8 carbons in the alkyl residue, such as e.g. methyl and butyl glucoside;
sugar alcohols with 5 to 12 carbon atoms, such as e.g. sorbitol or mannitol,
sugars with 5 to 12 carbon atoms, such as e.g. glucose or saccharose;
amino sugars such as e.g. glucamine;
dialcohol amines such as diethanolamine or 2-amino-1,3-propanediol.

Preservatives

Examples of suitable preservatives include phenoxyethanol, formaldehyde solution, parabens, pentanediol or sorbic acid, as well as the silver complex under the name Surfacine® and the further substance classes listed in Attachment 6, Sections A and B of the Cosmetics Regulation.

Perfume Oils and Aromas

As perfume oils, one can mention mixtures of natural and synthetic fragrances. Natural fragrances are extracts of flowers (lily, lavender, rose, jasmine, neroli, ylang-ylang), stems and leaves (geranium, patchouli, petitgrain), fruits (anis, coriander, caraway seeds, juniper berry), fruit peels (bergamot, lemon, orange), roots (mace, angelica, celery, cardamom, costus, iris, calmus), woods (pine, sandal, guaiac, cedar, rosewoods), herbs and grasses (tarragon, lemon grass, sage, thyme), needles and branches (spruce, fir, pine, mountain pine), resins and balsams (galbanum, elemi, benzoin, myrrh, olibanumum, opopanax). Also suitable are animal raw materials, such as e.g. civet and castoreum. Typical synthetic fragrance compounds are products of the ester, ether, aldehyde, ketone, alcohol, and hydrocarbon type. Fragrance compounds of the ester type are e.g. benzyl acetate, phenoxyethylisobutyrate, p-tert-butylcyclohexyl acetate, linalyl acetate, dimethylbenzylcarbinyl acetate, phenylethyl acetate, linalyl benzoate, benzyl formiate, ethylmethylphenyl glycinate, allylcyclohexyl propionate, styrallyl propionate, and benzyl salicylate. Examples of ethers are e.g. benzylethyl ether, and examples of aldehydes are e.g. linear alkanals with 8 to 18 carbon atoms, citral, citronellal, citronellyloxyacetaldehyde, cyclamen aldehyde, hydroxycitronellal, lilial, and bourgeonal, examples of the ketones are e.g. the ionones, α-isomethyl ionone and methyl cedryl ketone, examples of the alcohols are anethol, citronellol, eugenol, isoeugenol, geraniol, linalool, phenylethyl alcohol and terpineol, and examples of the hydrocarbons are mainly the terpenes and balsams. Preferred, however, is the use of mixtures of different fragrances, which together produce a pleasant scent. Ethereal oils of lower volatility, which are mostly used as aroma components, are also suitable as perfume oils, e.g. sage oil, camomile oil, clove oil, melissa oil, mint oil, cinnamon leaf oil, linden flower oil, juniper berry oil, vetiver oil, olibanum oil, galbanum oil, labolanum oil and lavandin oil. Preferably, bergamot oil, dihydromyrcenol, lilial, lyral, citronellol, phenylethyl alcohol, α-hexyl cinnamaldehyde, geraniol, benzyl acetone, cyclamen aldehyde, linalool, boisambrene forte, ambroxan, indole, gedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat are used, individually or in mixtures.

Suitable aromatic agents include peppermint oil, spearmint oil, aniseed oil, star aniseed oil, caraway seed oil, eucalyptus oil, fennel oil, lemon oil, wintergreen oil, clove oil, menthol and the like.

Dyes

Substances that are suitable and approved for cosmetic purposes may be used, such as listed for example in the publication "Cosmetic Dyes" of the Dye Commission of the German Research Association, Verlag Chemie, Weinheim, 1984, pp. 81-106. Examples are cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and alizarin red (C.I. 58000). Luminol may also be included as a luminescent dye. These dyes are ordinarily used in concentrations of 0.001 to 0.1 wt % with respect to the mixture as a whole.

The total amount of the auxiliaries and additives can be 1 to 50, and preferably 5 to 40 wt % with respect to the agents in question. The agents may be manufactured by means of common cold or hot processes; the phase inversion temperature method is preferably used.

Food Preparations

A further object of the invention concerns food preparations, comprising
(a) amides of formula (I),
(b) menthol and/or menthol compounds of formulas (II), (III) and/or (IV) or aromatic substances, as well as
(c) a carrier approved for food purposes.

The carrier may be selected from the group composed of water, ethanol and glycerol.

The food preparations should preferably be beverages, dairy products, baked goods, and in particular chewing gums and bonbons.

The preparations according to the invention may contain the components (a) and (b) in a ratio by weight of 0.1:99 to 99.9:1, particularly 10:90 to 90:10, more preferably 25:75 to 75:25, and particularly preferably 40:60 to 60:40. The components (a+b) and (c) may be contained in a ratio by weight of 0.01:99.9 to 2:98, preferably 0.5:99.5 to 1.5:98.5, and particularly preferably about 1:99. The total content of the components (a+b) in the final products may be between 1 and 5,000, preferably 10 to 4,000, and particularly preferably 100 to 1,000 ppm.

Chewing Gums

Preferred food preparations, which contain as flavorings mixtures of the amides and menthol or the menthol compounds, are chewing gums. These products typically comprise water-insoluble and water-soluble components.

Water-Insoluble Base

The water-insoluble base, also referred to as the "gum base", ordinarily comprises natural or synthetic elastomers, resins, fats and oils, softeners, fillers, dyes, and optionally waxes. The amount of the base with respect to the total composition is ordinarily 5 to 95, preferably 10 to 50, and particularly preferably 20 to 35 wt %. In a typical embodiment of the invention, the base is composed of 20 to 60 wt % synthetic elastomers, 0 to 30 wt % natural elastomers, 5 to 55 wt % softeners, 4 to 35 wt % fillers and in secondary amounts, additives such as dyes, antioxidants, and the like, with the proviso that they are water-soluble in small amounts if applicable.

Examples of suitable synthetic elastomers include polyisobutylenes with average molecular weights (according to GPC) of 10,000 to 100,000, and preferably 50,000 to 80,000, isobutylene-isoprene copolymers ("butyl elastomers"), styrene-butadiene copolymers (styrene:butadiene ratio e.g. 1:3 to 3:1), polyvinyl acetates with average molecular weights (according to GPC) of 2,000 to 90,000, and preferably 10,000 to 65,000, polyisoprenes, polyethylene, vinyl acetate-vinyl laurate copolymers and mixtures thereof. Examples of suitable natural elastomers are rubbers such as smoked or liquid latex or guayule, as well as natural gums such as jelutong, lechi caspi, perillo, sorva, massaranduba balata, massaranduba chocolate, nispero, rosindinba, chicle, gutta hang hang, as well as mixtures thereof. The selection of the synthetic and natural elastomers and their mixing ratios essentially depends on whether the chewing gums are intended for blowing bubbles ("bubble gums") or not. Preferably, elastomer mixtures are used that contain jelutong, chicle, sorva and massaranduba.

In most case, the elastomers are found in processing to be too hard or insufficiently malleable, so it has been found to be advantageous to include special softeners, which of course must in particular meet all requirements for approval as food additives. In this respect, it is primarily esters of resin acids that are suitable, for example esters of lower aliphatic alcohols or polyols with fully or partially hydrogenated monomers or oligomeric resin acids. In particular, methyl, glycero-, or pentarerythritol esters, as well as mixtures thereof, are used for this purpose. Alternatively terpene resins that can be derived from alpha-pinene, beta-pinene, delta-limonene or mixtures thereof are also suitable.

As fillers or texturizers, magnesium or calcium carbonate, ground pumice, silicates, particularly magnesium or aluminum silicates, clays, aluminum oxides, talc, titanium dioxide, mono-, di- and tricalciumphosphate, as well as cellulose polymers, are suitable.

Suitable emulsifiers are tallow, hydrogenated tallow, hydrogenated or partially hydrogenated vegetable oils, cocoa butter, partial glycerides, lecithin, triacetin and saturated or unsaturated fatty acids with 6 to 22 and preferably 12 to 18 carbon atoms, as well as mixtures thereof.

For example, suitable dyes and whiteners are FD and C types and plant and fruit extracts approved for use as food dyes, as well as titanium dioxide.

Base compositions may contain waxes or be wax-free; examples of wax-free compositions can be found inter alia in the U.S. Pat. No. 5,286,500, the content of which is incorporated herein by reference.

Water-Soluble Components

In addition to the water-insoluble gum base, chewing gum preparations regularly contain a water-soluble component that is composed for example of softeners, sweeteners, fillers, flavorings, flavor enhancers, emulsifiers, dyes, acidifying agents, antioxidants and the like, here with the proviso that the components show at least sufficient water-solubility. Depending on the water-solubility of the particular component, individual components may therefore be part of either the water-insoluble or the water-soluble phase. However, it is also possible to use combinations, for example of a water-soluble and a water-insoluble emulsifier, wherein the individual components are then in different phases. Ordinarily, the water-insoluble portion accounts for 5 to 95, and preferably 20 to 80 wt % of the composition.

Water-soluble softeners or plasticizing agents are added to the chewing gum compositions in order to improve chewability and the chewing sensation, and are typically present in the mixture in amounts of 0.5 to 15 wt %. Typical examples are glycerol, lecithin, as well as aqueous solutions of sorbitol, hydrogenated starch hydrolysates, or corn syrup.

Both sugar-containing and sugar-free compounds are suitable as sweeteners, which are used in amounts of 5 to 95, preferably 20 to 80, and particularly preferably 30 to 60 wt % with respect to the chewing gum composition. Typical saccharide sweeteners are sucrose, dextrose, maltose, dextrin, dried invert sugar, fructose, levulose, galactose, corn syrup, as well as mixtures thereof. Suitable sugar substitutes are sorbitol, mannitol, xylitol, hydrogenated starch hydrolysate, maltitol and mixtures thereof. Also suitable as additives are the sweeteners referred to as HIAS ("High Intensity Artificial Sweeteners"), such as e.g. sucralose, aspartame, acesulfame salts, alitam, saccharin and saccharin salts, cyclamic acid and salts thereof, glycyrrhizins, dihydrochalcones, thaumatin, monellin and the like, individually or in blends.

The hydrophobic HIAS, which are the object of International Patent Application WO 2002 091849 A1 (Wrigley's), as well as stevia extracts and active components thereof, particularly ribeaudioside A, are particularly effective. The amount of these substances used depends primarily on their performance and is typically in the range of 0.02 to 8 wt %.

Particularly suitable for the production of low-calorie chewing gums are fillers such as e.g. polydextrose, raftilose, raftiline, fructooligosaccha rides (NutraFlora), palatinose oligosaacchharides, guar gum hydrolysate (Sun Fiber), and dextrins.

The selection of further flavorings is virtually unlimited and uncritical for the essence of the invention. Ordinarily, the total amount of all flavorings is 0.1 to 15, and preferably 0.2 to 5 wt % with respect to the chewing gum composition. Examples of other suitable flavorings include essential oils, synthetic flavorings and the like, such as e.g. aniseed oil, star aniseed oil, caraway seed oil, eucalyptus oil, fennel oil, lemon oil, wintergreen oil, clove oil, and the like, such as those used for example in oral and dental care products.

Moreover, the chewing gums may contain auxiliaries and additives that are suitable for example for dental care, particularly for fighting plaque and gingivitis, such as e.g. chlorhexidine, CPC, or trichlosan. pH-regulators (e.g. buffers or urea), anti-cavity agents (e.g. phosphates or fluorides), and biogenic agents (antibodies, enzymes, caffeine, plant extracts) may be included, provided these substances are approved for use in foods and do not interact with one another in an unfavorable manner.

Capsules

The preparations of the special amides and menthol or the menthol compounds, individually or in finished, fabricated cosmetic, pharmaceutical and food preparations, may also be prepared in capsule form. In addition to common macrocapsules based on gelatin, the type referred to as micro- or nanocapsules is suitable. These are understood by the person having ordinary skill in the art to include spherical aggregates with a diameter in the range of about 0.0001 to about 5 and preferably 0.005 to 0.5 mm that contain at least one solid or liquid core that is enclosed in at least one continuous shell. More precisely, these are finely-dispersed liquid or solid phases enclosed by film-forming polymers which, during manufacturing, precipitate on the material to be enclosed after emulsification and coacervation or interfacial polymerization. According to another process, molten waxes are absorbed into a matrix (a "microsponge", and these waxes may additionally be enclosed as microparticles in film-forming polymers. According to a third process, particles are alternately coated with polyelectrolytes having varying charges (the "layer-by-layer" process). The microscopically small capsules can be dried as a powder. In addition to single-core microcapsules, multi-core aggregates, also referred to as microspheres, are known, which contain two or more cores distributed in continuous shell material. Single- or multicore microcapsules may also be enclosed in an additional second, third, etc. shell. The shell may consist of natural, semisynthetic, or synthetic materials. Examples of natural shell materials are gum arabic, agar-agar, agarose, maltodextrins, alginic acid, or salts thereof, e.g. sodium or calcium alginate, fats and fatty acids, cetyl alcohol, collagen, chitosan, lecithins, gelatin, albumin, shellac, polysaccharides such as starch or dextrane, polypeptides, protein hydrolysates, sucrose, and waxes. Semi-synthetic shell materials include chemically modified celluloses, particularly cellulose esters and ethers, e.g. cellulose acetate, ethyl cellulose, hydroxypropyl cellulose, hydroxypropylmethyl cellulose, and carboxymethyl cellulose, as well as starch derivatives, particularly starch ether and esters. Synthetic shell materials are for example polymers such as polyacrylates, polyamides, polyvinyl alcohol or polyvinylpyrrolidone. Examples of microcapsules of prior art are the following commercial products (the respective shell materials are indicated in parentheses): Hallcrest Microcapsules (gelatin, gum arabic), Coletico Thalaspheres (maritime collagen), Lipotec Millicapseln (alginic acid, agar-agar), Induchem Unispheres (lactose, microcrystalline cellulose, hydroxypropylmethyl cellulose); Unicerin C30 (lactose, microcrystalline cellulose, hydroxypropylmethyl cellulose), Kobo glycospheres (modified starch, fatty acid esters, phospholipids), Softspheres (modified agar-agar) and Kuhs Probiol Nanospheres (phospholipids), as well as Primaspheres and Primasponges (chitosan, alginates) and Primasys (phospholipids). Particularly interesting for the encapsulation of preparations for cosmetic use are coacervates of cationic polymers, particularly of chitosan, with anionic polymers, particularly alginates. Corresponding processes are described for example in the documents WO 2001001926, WO 2001 001927, WO 2001 001928, and WO 2001 001929 (Cognis).

Gel-Forming Agents

Microcapsules are frequently the agents dissolved or dispersed in a gel phase. Preferred as gel-forming agents are substances that show the property of forming gels in aqueous solution at temperatures above 40° C. Typical examples of these are heteropolysaccharides and proteins. Preferred as thermogelling heteropolysaccharides are agaroses, which in the form of agar-agar obtained from red algae may also be present with up to 30 wt % of non-gel-forming agaropectin. The main components of the agaroses are linear polysaccharides of D-galactose and 3,6-anhydro-L-galactose, which are alternatingly bonded at β-1,3 and β-1,4. The heteropolysaccharides preferably have a molecular weight in the range of 110,000 to 160,000, and are both colorless and tasteless. Suitable alternatives are pectins, xanthans (including xanthan Gum), and mixtures thereof. Moreover, preferred types still form gels in a 1 wt % aqueous solution that do not melt below 80'C and resolidify above 40° C. Examples of the group of the thermogelling proteins are the various types of gelatin.

Cationic Polymers

Suitable cationic polymers include cationic cellulose derivatives, such as e.g. a quaternized hydroxyethyl cellulose available from Amerchol under the name Polymer JR 400®, cationic starch, copolymers of diallylammonium salts and acrylamides, quaternized vinylpyrrolidone/vinylimidazole polymers, such as e.g. Luviquat® (BASF), condensation products of polyglycols and amines, quaternized collagen polypeptides such as e.g. lauryl dimonium hydroxypropyl hydrolyzed collagen (Lamequat® L/Grunau), quaternized wheat polypeptides, polyethyleneimine, cationic silicone polymers such as e.g. amodimethicone, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), polyaminopolyamides, as well as crosslinked water-soluble polymers thereof, cationic chitin derivatives such as e.g. quaternized chitosan, optionally in microcrystalline dispersion form, condensation products of dihalogenalkylenes such as e.g. dibromobutane with bisdialkylamines such as e.g. bis-dimethylamino-1,3-propane, cationic guar gums such as e.g. Jaguar® CBS, Jaguar® C-17, Jaguar® C-16 produced by Celanese, and quaternized ammonium salt polymers such as e.g. Mirapol® A-15, Mirapol® AD-1, Mirapol® AZ-1 produced by Miranol. Chitosan is preferably used as an encapsulation material.

Chitosans constitute biopolymers and are classified in the group of the hydrocolloids. From a chemical standpoint, these are partially deacetylate chitins of differing molecular weights that comprise the following-idealized-monomer component:

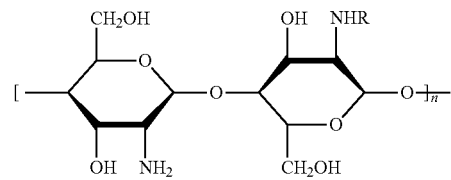

In contrast to most hydrocolloids, which are negatively charged in the range of biological pH values, chitosans are cationic biopolymers under these conditions. The positively charged chitosans may interact with surfaces of the opposite charge, and are therefore used in cosmetic hair and body care products, as well as pharmaceutical preparations. The starting material for the production of chitosan is chitin, preferably from the shell residues of crustaceans, which are available in large amounts as cheap raw materials. In this case, in a process first described by Hackmann et al., the chitin is ordinarily first deproteinized by adding bases, then demineralized by adding mineral acids, and finally deacylated by adding strong bases, wherein the molecular weights may be spread over a broad spectrum. The types used should preferably have an average molecular weight of 10,000 to 500,000 or 800,000 to 1,200,000 daltons and/or a viscosity according to Brookfield (1 wt % in glycolic acid) of below 5,000 mPas, a degree of deacetylation in the range of 80 to 88%, and an ash content of less than 0.3 wt %. As a rule, in order to improve water solubility, chitosans are used in form of their salts, preferably as glycolates.

Anionic Polymers

The purpose of the anionic polymers is to form membranes with cationic polymers. For this purpose, salts of alginic acid are particularly suitable. Alginic acid is a mixture of carboxyl-groups-containing polysaccharides with the following idealized monomer component:

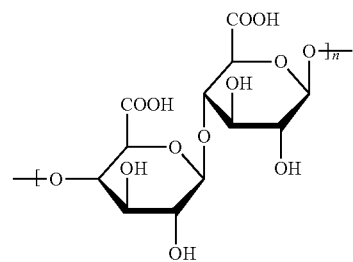

The average molecular weight of the alginic acids or the alginates is in the range of 150,000 to 250,000. In this case, salts of alginic acid are to be understood as both the complete and partial neutralization products thereof, particularly the alkali salts, and among these, preferably sodium alginate ("algin"), as well as the ammonium and alkaline earth salts. Particularly preferred are mixed alginates such as e.g. sodium/magnesium or sodium/calcium alginates. In an alternative embodiment of the invention, however, anionic chitosan derivatives, such as e.g. carboxylation and in particular succinylation products, are also suitable for this purpose. Alternatively, poly(meth)acrylates with average molecular weights in the range of 5,000 to 50,000 daltons, as well as the various carboxymethyl celluloses, are also suitable. Instead of anionic polymers, anionic surfactants or low molecular weight inorganic salts such as e.g. pyrophosphates may also be used to form the shell membrane.

Encapsulation

In order to manufacture microcapsules, one ordinarily takes a 1 to 10, and preferably a 2 to 5 wt % aqueous solution of the gel-forming agents, preferably agar-agar, and heats this under reflux. When the solution boils, preferably at 80 to 100° C., a second aqueous solution is added that contains the cationic polymer, preferably chitosan, in amounts of 0.1 to 2, and preferably 0.25 to 0.5 wt % and the agents in amounts of 0.1 to 25, and particularly preferably 0.25 to 10 wt %; this mixture is called the matrix. Loading of the microcapsules with the agents can also be 0.1 to 25 wt % with respect to the capsule weight. If desired, water-insoluble components such as inorganic pigments may also be added at this time to adjust the viscosity, with these being added as a rule in the form of aqueous or aqueous/alcoholic dispersions. In order to emulsify or disperse the active ingredients, it can further be beneficial to add to the matrix emulsifiers and/or solubilizers. After production of the matrix from gel-forming agents, cationic polymers, and active ingredients, the matrix may optionally be very finely dispersed in an oil phase with strong shear in order to produce the smallest possible particles in the subsequent encapsulation. In this case, it has been found to be particularly advantageous to heat the matrix to temperatures in the range of 40 to 60° C. while the oil phase is cooled to 10 to 20° C. In the final step, which is compulsory, the actual encapsulation takes place, i.e. the formation of the shell membrane by bringing the cationic polymer in the matrix into contact with the anionic polymers. For this purpose, it is recommended to treat the matrix, which is optionally dispersed in the oil phase, at a temperature in the range of 40 to 100, and preferably 50 to 60° C., with an approx. 1 to 50 and preferably 10 to 15 wt % aqueous solution of the anionic polymer, and in this process—if necessary—to remove the oil phase simultaneously or subsequently. As a rule, the aqueous preparations resulting from this process show a microcapsule content in the range of 1 to 10 wt %. In many cases, it can be advantageous if the solution of the polymers contains other ingredients, for example emulsifiers or preservatives. After filtration, microcapsules are obtained that show an average diameter preferably in the range of about 0.01 to 1 mm. It is recommended to screen the capsules in order to ensure that the size distribution is as uniform as possible. Although the microcapsules obtained in this manner may show any form desired, within the limits imposed by production, they are preferably approximately spherical. Alternatively, the anionic polymers may also be used to produce the matrix, and encapsulation may be carried out with the cationic polymers, particularly the chitosans.

Alternatively, encapsulation may also take place under exclusive use of cationic polymers, thus taking advantage of the property of these polymers of coagulating at pH values above the pKs value.

In a second alternative process, in order to produce the microcapsules according to the invention, an O/W emulsion is first prepared, which in addition to the oil component, water, and the agents, also contains an effective amount of an emulsifier. In order to prepare the matrix, this composition is mixed with a corresponding amount of an aqueous anionic polymer solution while stirring vigorously. Membrane formation is carried out by adding the chitosan solution. The entire process preferably takes place in the weakly acidic range of pH=3 to 4. If necessary, the pH can be adjusted by adding mineral acids. After membrane formation, the pH value is increased to 5 to 6, for example by adding triethanolamine or another base. This causes an increase in the viscosity, which can be further supported by adding more thickeners, such as e.g. polysaccharides, particularly xanthan gum, guar-guar, agar-agar, alginates and tyloses, carboxymethyl cellulose and hydroxyethyl cellulose, high-molecular-weight polyethylene glycol mono- and diesters of fatty acids, polyacrylates, polyacrylamides, and the like. Finally the microcapsules are separated from the aqueous phase, for example by decanting, filtration, or centrifugation.

In a third alternative process, formation of the microcapsules takes place around a preferably solid, for example a crystalline core, with the core being enclosed layer by layer by oppositely charged polyelectrolytes. In this connection, we refer to European Patent EP 1064088 B1 (Max-Planck Gesellschaft).

Application of the Preparations

Finally, the invention also concerns the application of mixtures containing
(a) amides of formula (I) and
(b) menthol and/or menthol compounds of formulas (II), (III) and/or (IV) or aromatic substances for the manufacture of cosmetic preparations, pharmaceutical preparations, as well as food preparations wherein the total content of the components (a+b) in the final products is preferably between 1 and 5,000, more preferably 10 to 4,000 and particularly preferably 100 to 1,000 ppm.

EXAMPLES

Examples 1 Through 7, Comparison Examples V1 to V4

Chewing gum compositions made up of 20 wt % polyisobutylene (MW 60,000), 51 wt % sorbitol, 5 wt % mannitol, 8 wt % glycerol, 8.2 wt % of a 1:1 mixture of Lycasin and glycerol, 0.2 wt % lecithin (water ad 99.5 wt %) were produced and mixed with 0.5 wt % each of various cooling agents. The chewing gum compositions were than subjected to sensory evaluation by a panel consisting of 5 trained persons on a scale from 1 (barely noticeable) to 10 (dominant). The composition of the cooling agents, as well as the evaluation of the individual taste and scent ratings (the average value of the evaluations is given in each case) are summarized in Table 1. Examples 1 to 7 are according to the invention, with Examples V1 to V4 serving as comparisons.

TABLE 1

Sensory evaluation of chewing gums with respect to cooling agents

| Cooling agent | 1 | 2 | 3 | 4 | 5 | 6 | 7 | V1 | V2 | V3 | V4 |
|---|---|---|---|---|---|---|---|---|---|---|---|
| Menthone glyceryl acetal | 10 | 30 | 50 | 90 | — | — | — | 100 | — | — | — |
| Menthyl lactate | — | — | — | — | 25 | 50 | 75 | — | 100 | — | — |
| Structure A24 | — | — | — | — | 75 | 50 | 25 | — | — | 100 | — |

TABLE 1-continued

Sensory evaluation of chewing gums with respect to cooling agents

| Cooling agent | 1 | 2 | 3 | 4 | 5 | 6 | 7 | V1 | V2 | V3 | V4 |
|---|---|---|---|---|---|---|---|---|---|---|---|
| Structure A194 | 90 | 70 | 50 | 10 | — | — | — | — | — | — | 100 |
| Evaluation | | | | | | | | | | | |
| Sweet | 4 | 5 | 6 | 5 | 5 | 6 | 6 | 4 | 3 | 3 | 3 |
| Hay-like/minty | 7 | 8 | 9 | 8 | 7 | 9 | 9 | 6 | 5 | 2 | 2 |
| Spicy | 3 | 3 | 3 | 3 | 4 | 3 | 3 | 5 | 5 | 7 | 7 |
| Pungent | 2 | 2 | 3 | 3 | 3 | 3 | 3 | 5 | 5 | 7 | 6 |
| Bitter | 2 | 2 | 2 | 2 | 9 | 2 | 2 | 4 | 4 | 4 | 5 |
| Tar-like | 2 | 2 | 2 | 2 | 2 | 2 | 2 | 4 | 5 | 4 | 3 |

Structure A24: N-phenyl-N-(thiophen-2-ylmethyl)-2(m-tolyloxy)acetamide

Structure A194: $\varepsilon$-3-(2,2-difluorobenzo[d][1,3]dioxol-5-yl)-N-ethyl-N-(thiohen-2-ylmethyl)acrylamide In sensory evaluation, all of the formulations according to the invention showed results clearly superior to the comparison products; specifically, the formulations tasted sweet rather than bitter, the tar taste was almost completely masked, and the unpleasant spicy-pungent odor was clearly reduced.

Examples 8 to 14, Comparison Examples V5 to V8

Various clear O/W sunscreen emulsions were produced according to the PIT method by mixing the components according to Table 2:

TABLE 2

Composition of O/W sunscreen lotions

| Components | Commercial product | Amount [wt %] |
|---|---|---|
| Polyglyceryl-2-polyhydroxystearate (and) lauryl glucosides (and) glycerol | Eumulgin ® VL 75 | 2.5 |
| Glyceryl stearate | Cutina ® GMS | 2.0 |
| Cetostearyl alcohol | Lanette ® O | 4.0 |
| PVP/hexadecene copolymer | Antaron ® V216 | 3.0 |
| Cocoglycerides | Myritol ® 818 | 6.0 |
| Oleyl erucate | Cetiol ® J600 | 3.0 |
| Dicaprylyl ether | Cetiol ® OE | 5.0 |
| Mineral oil | | 2.0 |
| Bisabolol | | 1.2 |

TABLE 2-continued

Composition of O/W sunscreen lotions

| Components | Commercial product | Amount [wt %] |
|---|---|---|
| Tocopherol | Copherol ® F 1300 | 1.0 |
| Octocrylene | Neo Heliopan ® 303 | 4.0 |
| Isoamyl-p-methoxycinnamate | Neo Heliopan ® E 1000 | 2.0 |
| Octyl methoxycinnamate | Neo Heliopan ® AV | 3.0 |
| Octyl triazone | Uvinul ® T15 | 1.0 |
| Cooling agent | | 0.5 |
| Glycerol | | 5.0 |
| Water | | Ad 100 |

The sunscreen lotions differed only with respect to the cooling agents, which in one case were various methyl compounds individually and in (1:1) mixtures with 2-(2-isopropyl-5-methylphenoxy)-N-(1H-pyrazol-3-yl)-N-(thiophen-2-yl)-methylacetamide (structure A86).

After being produced, the lotions were placed in clear PET bottles and stored at 30° C. The lotions were then evaluated for appearance after 12, 24, and 48 h. In this example, (+)=unchanged; (#)=minor droplet formation, and (−)=precipitation of oil droplets on the surface, accompanied by slight yellow discoloration. The results are summarized in Table 3. Examples 8 to 14 are according to the invention, with Examples V5 to V8 again serving as comparisons. The preparations according to the invention show clearly improved stability.

TABLE 3

Evaluation of storage stability of O/W sunscreen lotions in with respect to cooling agents

| Cooling agent | 8 | 9 | 10 | 11 | 12 | 13 | 14 | V5 | V6 | V7 | V8 |
|---|---|---|---|---|---|---|---|---|---|---|---|
| Menthone glyceryl acetal | 20 | 50 | 60 | 70 | 80 | — | — | 100 | — | — | — |
| Menthyl lactate | — | — | — | — | — | 50 | — | — | 100 | — | — |
| Menthol methyl ether | — | — | — | — | — | — | 50 | — | — | 100 | — |
| Structure A86 | 80 | 50 | 40 | 30 | 20 | 50 | 50 | — | — | — | 100 |
| Evaluation | | | | | | | | | | | |
| After 12 h | + | + | + | + | + | + | + | # | # | # | # |
| After 24 h | + | + | + | + | + | + | + | − | − | − | − |
| After 48 h | # | + | # | # | # | + | + | − | − | − | − |

The following tables show numerous formulation examples for cosmetic, pharmaceutical, and food preparations.

TABLE 4

Examples of cosmetic preparations (water, preservatives ad 100 wt %)

| Composition (INCI) | 1 | 2 | 3 | 4 | 5 | 6 | 7 | 8 | 9 | 10 |
|---|---|---|---|---|---|---|---|---|---|---|
| Texapon ® NSO Sodium laureth sulfate | — | — | — | — | — | — | 38.0 | 38.0 | 25.0 | — |
| Texapon ® SB 3 Disodium laureth sulfosuccinate | — | — | — | — | — | — | — | — | 10.0 | — |
| Plantacare ® 818 Coco glucosides | — | — | — | — | — | — | 7.0 | 7.0 | 6.0 | — |
| Plantacare ® PS 10 Sodium laureth sulfate (and) coco glucosides | — | — | — | — | — | — | — | — | — | 16.0 |
| Dehyton ® PK 45 Cocamidopropyl betaine | — | — | — | — | — | — | — | — | 10.0 | — |
| Dehyquart ® A Cetrimonium chloride | 2.0 | 2.0 | 2.0 | 2.0 | 4.0 | 4.0 | — | — | — | — |
| Dehyquart L ® 80 Dicocoylmethylethoxymonium methosulfate (and) propylene glycol | 1.2 | 1.2 | 1.2 | 1.2 | 0.6 | 0.6 | — | — | — | — |
| Eumulgin ® B2 Ceteareth-20 | 0.8 | 0.8 | — | 0.8 | — | 1.0 | — | — | — | — |
| Eumulgin ® VL 75 Lauryl glucoside (and) polyglyceryl-2 polyhydroxystearate (and) glycerol | — | — | 0.8 | — | 0.8 | — | — | — | — | — |
| Lanette ® O Cetostearyl alcohol | 2.5 | 2.5 | 2.5 | 2.5 | 3.0 | 2.5 | — | — | — | — |
| Cutina ® GMS Glyceryl stearate | 0.5 | 0.5 | 0.5 | 0.5 | 0.5 | 1.0 | — | — | — | — |
| Cetiol ® PGL Hexyldecanol (and) hexyldecyl laurate | — | 1.0 | — | — | 1.0 | — | — | — | — | — |
| Cetiol ® V Decyl oleate | — | — | — | 1.0 | — | — | — | — | — | — |
| Eutanol ® G Octyldodecanol | — | — | 1.0 | — | — | 1.0 | — | — | — | — |
| Lamesoft ® LMG Glyceryl laurate (and) potassium cocoyl hydrolyzed collagen | — | — | — | — | — | — | 3.0 | 2.0 | 4.0 | — |
| Euperlan ® PK 3000 AM Glycol distearate (and) laureth-4 (and) cocamidopropyl betaine | — | — | — | — | — | — | — | 3.0 | 5.0 | 5.0 |
| General ® 122 N Soy sterol | — | — | — | — | 1.0 | 1.0 | — | — | — | — |
| Frescolat MGA/Structure A88 (1:1) | 0.3 | 0.3 | 0.3 | 0.3 | 0.3 | 0.3 | 0.3 | 0.3 | 0.3 | 0.3 |
| Hydagen ® CMF Chitosan | 1.0 | 1.0 | 1.0 | 1.0 | 1.0 | 1.0 | 1.0 | 1.0 | 1.0 | 1.0 |
| Copherol ® 1250 Tocopherol acetate | — | — | 0.1 | 0.1 | — | — | — | — | — | — |
| Arlypon ® F Laureth-2 | — | — | — | — | — | — | 3.0 | 3.0 | 1.0 | — |
| Sodium chloride | — | — | — | — | — | — | — | 1.5 | — | 1.5 |

| Composition (INCI) | 11 | 12 | 13 | 14 | 15 | 16 | 17 | 18 | 19 | 20 |
|---|---|---|---|---|---|---|---|---|---|---|
| Texapon ® NSO Sodium laureth sulfate | 20.0 | 20.0 | 12.4 | — | 25.0 | 11.0 | — | — | — | — |
| Texapon ® K 14 S Sodium myreth sulfate | — | — | — | — | — | — | — | — | 11.0 | 23.0 |
| Texapon ® SB 3 Disodium laureth sulfosuccinate | — | — | — | — | — | 7.0 | — | — | — | — |
| Plantacare ® 818 Coco glucosides | 5.0 | 5.0 | 4.0 | — | — | — | — | — | 6.0 | 4.0 |
| Plantacare ® 2000 Decyl glucoside | — | — | — | 5.0 | 4.0 | — | — | — | — | — |

TABLE 4-continued

Examples of cosmetic preparations (water, preservatives ad 100 wt %)

| | | | | | | | | | | |
|---|---|---|---|---|---|---|---|---|---|---|
| Plantacare ® PS 10<br>Sodium laureth sulfate<br>(and) coco glucosides | — | — | — | 40.0 | — | — | 16.0 | 17.0 | — | — |
| Dehyton ® PK 45<br>Cocamidopropyl betaine | 20.0 | 20.0 | — | — | 8.0 | — | — | — | — | 7.0 |
| Eumulgin ® B1<br>Ceteareth-12 | — | — | — | — | 1.0 | — | — | — | — | — |
| Eumulgin ® B2<br>Ceteareth-20 | — | — | — | 1.0 | — | — | — | — | — | — |
| Lameform ® TGI<br>Polyglyceryl-3<br>isostearate | — | — | — | 4.0 | — | — | — | — | — | — |
| Dehymuls ® PGPH<br>Polyglyceryl-2<br>dipolyhydroxystearate | — | — | 1.0 | — | — | — | — | — | — | — |
| Monomuls ® 90-L 12<br>glyceryl laurate | — | — | — | — | — | — | — | — | 1.0 | 1.0 |
| Cetiol ® HE<br>PEG-7 glyceryl cocoate | — | 0.2 | — | — | — | — | — | — | — | — |
| Eutanol ® G<br>Octyldodecanol | — | — | — | 3.0 | — | — | — | — | — | — |
| Nutrilan ® keratin W<br>Hydrolyzed keratin | — | — | — | — | — | — | — | — | 2.0 | 2.0 |
| Nutrilan ® I<br>Hydrolyzed collagen | 1.0 | — | — | — | — | 2.0 | — | 2.0 | — | — |
| Lamesoft ® LMG<br>Glyceryl laurate (and)<br>potassium cocoyl<br>hydrolyzed collagen | — | — | — | — | — | — | — | — | 1.0 | — |
| Lamesoft ® 156<br>Hydrogenated tallow<br>glyceride (and)<br>potassium cocoyl<br>hydrolyzed collagen | — | — | — | — | — | — | — | — | — | 5.0 |
| Gluadin ® WK<br>Sodium cocoyl hydrolyzed<br>wheat Protein | 1.0 | 1.5 | 4.0 | 1.0 | 3.0 | 1.0 | 2.0 | 2.0 | 2.0 | — |
| Euperlan ® PK 3000 AM<br>Glycol distearate (and)<br>laureth-4 (and)<br>cocamidopropyl betaine | 5.0 | 3.0 | 4.0 | — | — | — | — | 3.0 | 3.0 | — |
| Arlypon ® F<br>Laureth-2 | 2.6 | 1.6 | — | 1.0 | 1.5 | — | — | — | — | — |
| Frescolat MGA/Structure<br>A88 (1:1} | 0.3 | 0.3 | 0.3 | 0.3 | 0.3 | 0.3 | 0.3 | 0.3 | 0.3 | 0.3 |
| Hydagen ® CMF<br>Chitosan | 1.0 | 1.0 | 1.0 | 1.0 | 1.0 | 1.0 | 1.0 | 1.0 | 1.0 | 1.0 |
| Sodium chloride | — | — | — | — | — | 1.6 | 2.0 | 2.2 | — | 3.0 |
| Glycerol (86 wt %) | — | 5.0 | — | — | — | — | — | 1.0 | 3.0 | — |

| Composition (INCI) | 21 | 22 | 23 | 24 | 25 | 26 | 27 | 28 | 29 | 30 |
|---|---|---|---|---|---|---|---|---|---|---|
| Texapon ® NSO<br>Sodium laureth sulfate | — | 30.0 | 30.0 | — | 25.0 | — | — | — | — | — |
| Plantacare ® 818<br>Coco glucosides | — | 10.0 | — | — | 20.0 | — | — | — | — | — |
| Plantacare ® PS 10<br>Sodium laureth sulfate<br>(and) coco glucosides | 22.0 | — | 5.0 | 22.0 | — | — | — | — | — | — |
| Dehyton ® PK 45<br>Cocamidopropyl betaine | 15.0 | 10.0 | 15.0 | 15.0 | 20.0 | — | — | — | — | — |
| Emulgade ® SE<br>Glyceryl stearate (and)<br>ceteareth 12/20 (and)<br>cetostearyl alcohol<br>(and) cetyl palmitate | — | — | — | — | — | 5.0 | 5.0 | 4.0 | — | — |
| Eumulgin ® B1<br>Ceteareth-12 | — | — | — | — | — | — | — | 1.0 | — | — |
| Lameform ® TGI<br>Polyglyceryl-3<br>isostearate | — | — | — | — | — | — | — | — | 4.0 | — |
| Dehymuls ® PGPH<br>Polyglyceryl-2<br>dipolyhydroxystearate | — | — | — | — | — | — | — | — | — | 4.0 |
| Monomuls ® 90-O 18<br>Glyceryl oleate | — | — | — | — | — | — | — | — | 2.0 | — |
| Cetiol ® HE<br>PEG-7 glyceryl cocoate | 2.0 | — | — | 2.0 | 5.0 | — | — | — | — | 2.0 |

TABLE 4-continued

Examples of cosmetic preparations (water, preservatives ad 100 wt %)

| Composition (INCI) | 21 | 22 | 23 | 24 | 25 | 26 | 27 | 28 | 29 | 30 |
|---|---|---|---|---|---|---|---|---|---|---|
| Cetiol ® OE / Dicaprylyl ether | — | — | — | — | — | — | — | — | 5.0 | 6.0 |
| Cetiol ® PGL / Hexyldecanol (and) hexyldecyl laurate | — | — | — | — | — | — | — | 3.0 | 10.0 | 9.0 |
| Cetiol ® SN / Cetostearyl isononanoate | — | — | — | — | — | 3.0 | 3.0 | — | — | — |
| Cetiol ® V / Decyl oleate | — | — | — | — | — | 3.0 | 3.0 | — | — | — |
| Myritol ® 318 / Coco caprylate caprate | — | — | — | — | — | — | — | 3.0 | 5.0 | 5.0 |
| Beeswax | — | — | — | — | — | — | — | — | 7.0 | 5.0 |
| Nutrilan ® elastin E20 / Hydrolyzed elastin | — | — | — | — | — | 2.0 | — | — | — | — |
| Nutrilan ® I-50 / Hydrolyzed collagen | — | — | — | — | 2.0 | — | 2.0 | — | — | — |
| Gluadin ® AGP / Hydrolyzed wheat gluten | 0.5 | 0.5 | 0.5 | — | — | — | — | 0.5 | — | — |
| Gluadin ® WK / Sodium cocoyl hydrolyzed wheat protein | 2.0 | 2.0 | 2.0 | 2.0 | 5.0 | — | — | — | 0.5 | 0.5 |
| Euperlan ® PK 3000 AM / Glycol distearate (and) laureth-4 (and) cocamidopropyl betaine | 5.0 | — | — | 5.0 | — | — | — | — | — | — |
| Arlypon ® F / Laureth-2 | — | — | — | — | — | — | — | — | — | — |
| Retinol | 1.0 | 1.0 | 1.0 | 1.0 | 1.0 | 1.0 | 1.0 | 1.0 | 1.0 | 1.0 |
| Hydagen ® CMF / Chitosan | 1.0 | 1.0 | 1.0 | 1.0 | 1.0 | 1.0 | 1.0 | 1.0 | 1.0 | 1.0 |
| Frescolat MGA/Structure A88 (1:1) | 0.3 | 0.3 | 0.3 | 0.3 | 0.3 | 0.3 | 0.3 | 0.3 | 0.3 | 0.3 |
| Glycerol (86 wt %) | — | — | — | — | — | 3.0 | 3.0 | 5.0 | 5.0 | 3.0 |

| Composition (INCI) | 31 | 32 | 33 | 34 | 35 | 36 | 37 | 38 | 39 | 40 |
|---|---|---|---|---|---|---|---|---|---|---|
| Dehymuls ® PGPH / Polyglyceryl-2 dipolyhydroxystearate | 4.0 | 3.0 | — | 5.0 | — | — | — | — | — | — |
| Lameform ® TGI / Polyglyceryl-3 diisostearate | 2.0 | 1.0 | — | — | — | — | — | — | — | — |
| Emulgade ® PL 68/50 / Cetostearylglucoside (and) cetostearyl alcohol | — | — | — | — | 4.0 | — | — | — | 3.0 | — |
| Eumulgin ®B2 / Ceteareth-20 | — | — | — | — | — | — | — | 2.0 | — | — |
| Tegocare ® PS / Polyglyceryl-3 methylglucose distearate | — | — | 3.0 | — | — | — | 4.0 | — | — | — |
| Eumulgin VL 75 / Polyglyceryl-2 dipolyhydroxystearate (and) lauryl glucoside (and) glycerol | — | — | — | — | — | 3.5 | — | — | 2.5 | — |
| Bees Wax | 3.0 | 2.0 | 5.0 | 2.0 | — | — | — | — | — | — |
| Cutina ® GMS / Glyceryl stearate | — | — | — | — | — | 2.0 | 4.0 | — | — | 4.0 |
| Lanette ® O / Cetostearyl alcohol | — | — | 2.0 | — | 2.0 | 4.0 | 2.0 | 4.0 | 4.0 | 1.0 |
| Antaron ® V 216 / PVP/hexadecene copolymer | — | — | — | — | — | 3.0 | — | — | — | 2.0 |
| Myritol ® 818 / Cocoglycerides | 5.0 | — | 10.0 | — | 8.0 | 6.0 | 6.0 | — | 5.0 | 5.0 |
| Finsolv ® TN / C12/15 alkyl benzoate | — | 6.0 | — | 2.0 | — | 3.0 | — | — | — | 2.0 |
| Cetiol ® J 600 / Oleyl erucate | 7.0 | 4.0 | 3.0 | 5.0 | 4.0 | 3.0 | 3.0 | — | 5.0 | 4.0 |
| Cetiol ® OE / Dicaprylyl ether | 3.0 | — | 6.0 | 8.0 | 6.0 | 5.0 | 4.0 | 3.0 | 4.0 | 6.0 |
| Mineral Oil | — | 4.0 | — | 4.0 | — | 2.0 | — | 1.0 | — | — |
| Cetiol ® PGL / Hexadecanol (and) hexyldecyl laurate | — | 7.0 | 3.0 | 7.0 | 4.0 | — | — | — | 1.0 | — |
| Bisabolol | 1.2 | 1.2 | 1.2 | 1.2 | 1.2 | 1.2 | 1.2 | 1.2 | 1.2 | 1.2 |
| Frescolat MGA/Structure A88 (1:1) | 0.3 | 0.3 | 0.3 | 0.3 | 0.3 | 0.3 | 0.3 | 0.3 | 0.3 | 0.3 |

TABLE 4-continued

| Examples of cosmetic preparations (water, preservatives ad 100 wt %) | | | | | | | | | | |
|---|---|---|---|---|---|---|---|---|---|---|
| Hydagen ® CMF Chitosan | 1.0 | 1.0 | 1.0 | 1.0 | 1.0 | 1.0 | 1.0 | 1.0 | 1.0 | 1.0 |
| Copherol ® F 1300 Tocopherol/tocopheryl acetate | 0.5 | 1.0 | 1.0 | 2.0 | 1.0 | 1.0 | 1.0 | 2.0 | 0.5 | 2.0 |
| Neo Heliopan ® hydro Sodium phenylbenzimidazole sulfonate | 3.0 | — | — | 3.0 | — | — | 2.0 | — | 2.0 | — |
| Neo Heliopan ® 303 Octocrylene | — | 5.0 | — | — | — | 4.0 | 5.0 | — | — | 10.0 |
| Neo Heliopan ® BB Benzophenone-3 | 1.5 | — | — | 2.0 | 1.5 | — | — | — | 2.0 | — |
| Neo Heliopan ® E 1000 isoamyl p-methoxycinnamate | 5.0 | — | 4.0 | — | 2.0 | 2.0 | 4.0 | 10.0 | — | — |
| Neo Heliopan ® AV Octyl methoxycinnamate | 4.0 | — | 4.0 | 3.0 | 2.0 | 3.0 | 4.0 | — | 10.0 | 2.0 |
| Uvinul ® T 150 Octyl triazone | 2.0 | 4.0 | 3.0 | 1.0 | 1.0 | 1.0 | 4.0 | 3.0 | 3.0 | 3.0 |
| Zinc Oxide | — | 6.0 | 6.0 | — | 4.0 | — | — | — | — | 5.0 |
| Titanium dioxide | — | — | — | — | — | — | — | 5.0 | — | — |
| Glycerol (86 wt %) | 5.0 | 5.0 | 5.0 | 5.0 | 5.0 | 5.0 | 5.0 | 5.0 | 5.0 | 5.0 |

(1-4) Hair rinse, (5-6) Hair treatment formula, (7-8) Shower bath formula, (9) Shower gel, (10) Wash lotion
(11-14) Shower bath "Two-in-One", (15-20) Shampoo
(21-25) Foam bath, (26) Soft creme, (27, 28) Moisturizing emulsion, (29, 30) Night creme
(31) W/O Sunscreen creme, (32-34) W/O Sunscreen lotion, (35, 38, 40) O/W Sunscreen lotion
(36, 37, 39) O/W Sunscreen creme Examples 15 to 19, Comparison Examples V9 to V11

In order to determine the reduction in apatite stability, a blind test was first conducted. For this purpose, a reaction vessel with 300 ml of desalinated water was temperature-controlled to 37° C., and 0.5 g of hydroxyapatite powder (spec. surface area 60 m²/g, Merck) was suspended therein. The pH value of the suspension was kept at a constant value of 5 by means of an automatic burette used to add lactic acid. The amount of 0.1 molar lactic acid consumed in order to stabilize the pH was registered with a recorder. The consumption of lactic acid registered after 2 hours was equivalent to the solubility of the untreated hydroxyapatite powder ($L_u$).

The test was then continued adding 50 or 150 mg of the active ingredient mixture to be tested. The consumption of lactic acid registered after 2 hours was equivalent to the solubility of the treated hydroxyapatite powder ($L_b$). The reduction in apatite solubility (ALR in %) caused by the active ingredient was calculated as follows:

$ALR\ (\%)=(L_u-L_b)*100/L_u\ (\%)$

The results of the measurements are summarized in Table 5.

In order to determine inhibition of crystal growth (KWI in %) by hydroxyapatite, a blind test was also first conducted. For this purpose, a reaction vessel with 400 ml of a 0.0008 molar solution of $KH_2PO_4$ and 45 ml of a 0.012 molar solution of $CaCl_2$ was prepared. This solution was adjusted to a pH of 7.4 by titration with a 0.05 molar solution of KOH. After a stable pH value had been maintained for at least 30 minutes, 100 mg of hydroxyapatite powder (spec. surface area 60 m²/g, Merck) was added. The pH value of the suspension was kept at a constant value of 7.4 by means of an automatic burette which can be used to add 0.05 molar KOH solution. The amount of 0.05 molar KOH solution consumed in order to stabilize the pH was registered with a recorder. The consumption of KOH solution ($K_u$) registered after 2 hours was equivalent to the formation of hydroxyapatite (growth of crystals in the suspension).

The test was then continued adding 6 or 30 mg of the active ingredient to be tested. The consumption of 0.05 molar KOH solution ($K_b$) registered after 2 hours was equivalent to the formation of hydroxyapatite (growth of crystals in the suspension) under the effect of the active ingredient. Inhibition of crystal growth by the active ingredient was calculated as follows:

$KWI\ (\%)=(K_u-K_b)*100/K_u\ (\%)$

The results of the measurements are summarized in Table 5.

TABLE 5

| Apatite solubility and crystal growth inhibition with respect to flavoring components | | | | | | | | |
|---|---|---|---|---|---|---|---|---|
| Composition cooling agent | 15 | 16 | 17 | 18 | 19 | V9 | V10 | V11 |
| Methyl lactate | 50 | | | | | 100 | | |
| Menthone glyceryl acetal | | 50 | | | | | 100 | |
| Menthol ethylene glycol carbonate | | | 50 | | | | | |
| Menthyl succinate | | | | 50 | | | | |
| WS-5 | | | | | 50 | | | |
| Structure A86 | 50 | 50 | 50 | 50 | 50 | | | 100 |
| Apatite solubility [%] | | | | | | | | |
| 30 mg | 10 | 11 | 10 | 9 | 8 | 5 | 6 | 5 |
| 150 mg | 12 | 26 | 21 | 20 | 20 | 12 | 13 | 14 |
| Crystal growth inhibition [%] | | | | | | | | |
| 5 mg | 14 | 19 | 17 | 15 | 16 | 10 | 9 | 11 |
| 6 mg | 17 | 36 | 30 | 31 | 29 | 14 | 17 | 16 |

Examples 15 to 19 show that the preparations according to the invention showed clearly higher apatite solubility and stronger inhibition of apatite crystal formation compared to the individual components. Oral care products and toothpastes containing such mixtures are characterized by better effectiveness against tartar formation.

Table 6 below shows a number of formulation examples for toothpastes and mouthwashes.

TABLE 6

| Component | Commercial product | Amount [wt %] |
|---|---|---|
| a Toothpaste composition | | |
| Precipitated silicic acid | Sident ® 12 DS | 18.0 |
| Thickening silicic acid | Aerosil ® 200 | 0.8 |
| Sorbitol | | 17.5 |
| Glycerol | | 17.5 |
| Carboxymethyl cellulose | Relatin ® 100 SR | 0.9 |
| Sodium lauryl sulfate | Texapon ® K1296 | 2.0 |
| Sodium fluoride | | 0.22 |
| Sodium saccharine | | 0.2 |
| Frecolat MAG/Structure A88 (1:1) | | 1.0 |
| Water | | Ad 100 |
| b Mouthwash composition | | |
| Ethanol (96%) | | 10.0 |
| Sorbitan monolaurate + 20EO | Tween ® 20 | 0.4 |
| Frescolat MAG/Structure A124 (1:1) | | 0.3 |
| Sorbitol (70% aqueous solution) | | 8.0 |
| p-Hydroxybenzoic acid methyl ester | | 0.2 |
| Water | | Ad 100 |

Structure A124: N-phenyl-N-(thiophen-2-ylmethyl)-2-(m-tolyloxy)acetamide

Finally, Table 7 summarizes a number of example formulations of toothpaste compositions.

TABLE 7

| Toothpaste compositions | | | | | | | | |
|---|---|---|---|---|---|---|---|---|
| Composition | A | B | C | D | E | F | G | H |
| Polyisobutylene (MW 20,000) | 30.0 | 30.0 | 30.0 | 40.0 | 20.0 | 20.0 | 25.0 | 30.0 |
| Glucose | 51.0 | 51.0 | 51.0 | 42.5 | | | | |
| Corn syrup | 10.0 | 10.0 | 10.0 | 8.0 | | | | |
| Sorbitol | | | | | 51.0 | 51.0 | 47.5 | 44.5 |
| Mannitol | | | | | 5.0 | 5.0 | 4.3 | 3.6 |
| Glycerol | 1.8 | 1.8 | 1.8 | 1.8 | 8.0 | 8.0 | 8.0 | 7.0 |
| Lycasin:glycerol (1:1) | | | | | 8.2 | 8.2 | 8.0 | 7.0 |
| Lecithin | | | | | 0.2 | 0.2 | 0.2 | 0.2 |
| Frescolat MAG/Structure A157 (1:1) | 1.0 | 1.0 | 1.0 | 1.0 | 1.0 | 1.0 | 1.0 | 1.0 |
| Water | | | | Ad 100 | | | | |

Structure A157: N-(pyridin-2-yl)-N-(thiophen-2-ylmethyl)-3-p-tolylpropanamide

The invention claimed is:

1. A composition comprising
   (i) component (a) selected from the group consisting of
      (a1) 2-(2-isopropyl-5-methylphenoxy)-N-(1H-pyrazol-3-yl)-N-(thiophen-2-yl)methylacetamide) having the formula

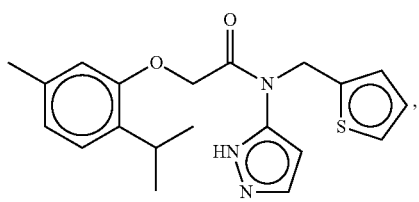

(a2) N-(1H-pyrazol-5-yl)-N-(thiophen-2-ylmethyl)-2-(p-tolyloxy)acetamide having the formula

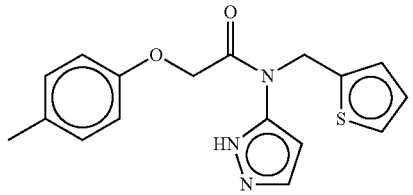

and mixtures thereof, and (ii) component (b) selected from the group consisting of menthol, menthone glyceryl ketal, menthol propylene glycol carbonate, menthyl-N-monomenthyl ethyloxamate, monomenthyl succinate, monomenthyl glutamate, menthoxy-1,2-propanediol, menthoxy-2-methyl-1,2-propanediol, the menthane carboxylic acid esters and amides having the following formulae

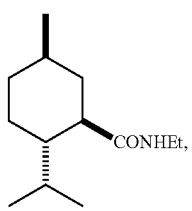
WS-3

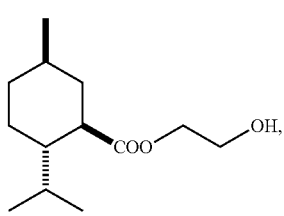
WS-4

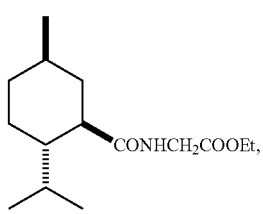
WS-5

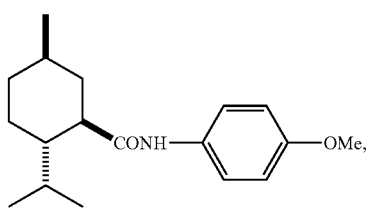
WS-12

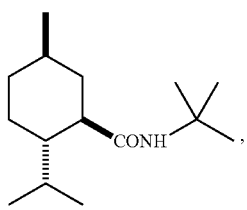
WS-14

-continued

WS-30

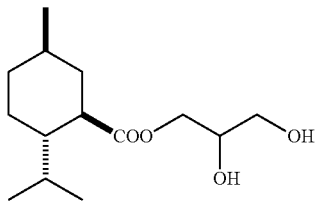

and mixtures thereof,
wherein components (a) and (b) are present in synergistically effective amounts.

2. The composition of claim 1, further comprising a cosmetic additive (component c) selected from the group consisting of surfactants, oils, emulsifiers, pearlescent waxes, consistency-enhancing agents, thickeners, superfatting agents, stabilizers, polymers, silicone compounds, fats, waxes, lecithins, phospholipids, UV light protection factors, humectants, biogenic agents, antioxidants, deodorants, antiperspirants, antidandruff agents, film-forming agents, swelling agents, insect repellents, self-tanning agents, tyrosine inhibitors, hydrotropes, solubilizers, preservatives, perfumed oils and dyes and mixtures thereof.

3. The composition of claim 1, further comprises at least one aromatic substance.

4. The composition of claim 3, wherein said aromatic substances are selected from the group consisting of anethol, acetanisole, acetaldehyde, acetylmethylcarbinol, 2-acetylpyrazine, 2-acetylpyridine, 2-acetylthiazoline, 2-acetylthiazole, allyl capronate, alpha-amylcinnamaldehyde, para-anisaldehyde, anis alcohol, dimethyl isopropyldithiazine, benzaldehyde, benzyl acetate, L-borneol, butyric acid, butyl acetate, 3-butylidene phtalide, capronic acid, carvacrol, L-carvone, d-carvone, carvomenthone, cis-carvyl acetate, caryophyllene, 1,8-cineol, 1,4-cineol, cinnamyl acetate, citral, citronellal, citronellol, citronellyl acetate, cumin aldehyde, cyclopentadecanolide, alpha-damascone, beta-damascone, alpha-damascenone, beta-damascenone, delta-decalactone, gamma-decalactone, dehydromenthofurolactone, dihydromenthofurolactone, 2,3-diethylpyrazine, dihydroanethol, dihydrocarvone, menthyl lactatedihydrocumarin, beta-dihydroionone, dimethyl anthranilate, dimethyl sulfide, dimethyl pyrazine, sotolone, diphenyl oxide, divanillin, 2,4-decadienal, delta-dodecalactone, gamma-dodecalactone, acetic acid, ethyl acetate, ethyl butyrate, ethyl 2-methylbutyrate, ethyl capronate, ethyl caprylate, ethyl cinnamate, ethyl isobutyrate, ethyl vanillin, ethyl lactate, ethyl maltol, ethyl methylthiopropionate, 4-ethylphenol, ethyl isovalerianate, eugenol, fenchol, furaneol, filbertone, frambinone, frambinone methylether, furfurylthiol, undecatriene, geraniol, geranyl acetate, geranyl isobutyrate, guaiacol, heliotropin, 2-heptanone, Z-4-heptenal, gamma-hexalactone, gamma-heptalactone, Z-3-hexenol, E-2-hexenol, hexanol, hexyl acetate, Z-3-hexenyl acetate, E-2-hexenyl acetate, alpha-hexyl cinnamaldehyde, Z-3-hexenyl capronate, hotrienol, indole, alpha-iron, alpha-ionone, beta-ionone, isoamyl acetate, isoamyl butyrate, isoamyl isovaerianate, isobutyl acetate, isobutyl thiazole, isobutyraldehyde, isovaleraldehyde, isoeugenol, isomenthone, isopropyl methoxypyrazine, isobutyl methoxypyrazine, 2,4-isopropyl methylpyrazine, isopulegol, jasmine lactone, cis-jasmone, camphor, ketoisophorone, cresole, d-limonene, L-linalool, D-linalool, linalyl acetate, linalool oxide, maltol, methylcyclopentenolone, L-menthone, D-menthone, L-menthol, D-menthol, neomenthol, L-menthyl acetate, D-menthyl acetate, massoia lactone, melonal, 1,8-menthene thiol, 1,8-epithiomenthane, 8,3-thiomenthanone, menthofurolactone, menthadienyl acetate, 2,3-methoxymethylpyrazine, methyl anthranilate, methyl salicylate, thymol, methyl butyrate, 2-methyl butylacetate, methyl cinnamate, 2,3-methylfuranthiol, 2,3-methyltetrahydrofuran thiol, methyl jasmonate, methyl dihydrojasmonate, methyl thiobutyrate, 1,3-methylthiohexylacetate, 1,3-methylthiohexanol, methional, myrtenal, naringin, neral, nerol, neryl acetate, gamma-nonalactone, delta-nonalactone, E-2-nonenal, Z-6-nonenal, Z-6-nonenol, nootkatone, dihydronootkatone, 1,3-octenol, gamma-octalactone, delta-octalactone, pellitorine, 1,3-pentenone, pentyl acetate, phenylacetaldehyde, phenylethyl alcohol, phenylethyl acetate, piperitanate, prenyl thiol, prenyl thioacetate, rose oxide, rubenamine, rubescenamine, sabinene hydrate, skatole, styrolyl acetate, terpineol, 4-terpinenol, 1,3-thiohexanol, 1,3-thiohexyl acetate, 4,4,2-thiopentanone, trimethylpyrazine, gamma and delta-undecalactone, 2,4-decadienal, 2,4-nonadienal, 2,6-nonadienal, 2,4-undecadienal, vanillin, vinyl guaiacol, whisky lactone, cinnamaldehyde, cinnamyl alcohol, diallyl dusulfide, allyl isothiocyanate, hexanal, E-2-hexenal, octanal, decanal, tridecatrienal, 12-methyltridecanal, alpha-pinene, beta-pinene, and piperitone and mixtures thereof.

5. The composition of claim 1, comprising components (a) and (b) in a ratio by weight of from 20:80 to 80:20.

6. The composition of claim 1, wherein component (b) is menthone glyceryl ketal.

7. A cosmetic, pharmaceutical or food preparation, comprising
(1) component (a1) of claim 1,
(2) component (b) of claim 1, and
(3) a carrier,
wherein components (a1) and (b) are present in synergistically effective amounts.

8. The cosmetic, pharmaceutical or food preparation of claim 7, wherein component (b) is menthol.

9. The cosmetic, pharmaceutical or food preparation of claim 7, wherein component (b) is selected from the group consisting of menthone glyceryl ketal, menthmeol propylene glycol carbonate, menthyl-N-ethyloxamate, monomenthyl succinate, monomenthyl glutamate, menthoxy-1,2-propanediol, menthoxy-2-methyl-1,2-propanediol and a mixture thereof.

10. The cosmetic, pharmaceutical or food preparation of claim 7, wherein component (b) is selected from the group consisting of menthane carboxylic acid esters and amides WS-3, WS-4, WS-5, WS-12, WS-14 and WS-30 and a mixture thereof.

11. The cosmetic, pharmaceutical or food preparation of claim 7, wherein the carrier is selected from the group consisting of water, alcohols with 2 to 6 carbon atoms, polyols with 1 to 10 carbon atoms and 2 to 4 hydroxyl groups and oils.

12. The cosmetic, pharmaceutical or food preparation of claim 7, further comprising at least one aromatic substance.

13. The cosmetic, pharmaceutical or food preparation composition of claim 7, comprising a product selected from the group consisting of skin care products, hair care products, body care products and sunscreen products.

14. A cosmetic, pharmaceutical or food preparation, comprising
(1) component (a2) of claim 1,
(2) component (b) of claim 1, and
(3) a carrier,
wherein components (a2) and (b) are present in synergistically effective amounts.

15. The cosmetic, pharmaceutical or food preparation of claim 14, wherein component (b) is menthol.

16. The cosmetic, pharmaceutical or food preparation of claim 14, wherein component (b) is selected from the group consisting of menthone glyceryl ketal, menthol propylene glycol carbonate, menthyl-N-ethyloxamate, monomenthyl succinate, monomenthyl glutamate, menthoxy-1,2-propanediol, menthoxy-2-methyl-1,2-propanediol and a mixture thereof.

17. The cosmetic, pharmaceutical or food preparation of claim 14, wherein component (b) is selected from the group consisting of menthane carboxylic acid esters and amides WS-3, WS-4, WS-5, WS-12, WS-14 and WS-30 and a mixture thereof.

18. The cosmetic, pharmaceutical or food preparation of claim 14, wherein the carrier is selected from the group consisting of water, alcohols with 2 to 6 carbon atoms, polyols with 1 to 10 carbon atoms and 2 to 4 hydroxyl groups and oils.

19. The cosmetic, pharmaceutical or food preparation of claim 14, further comprising at least one aromatic substance.

20. The cosmetic, pharmaceutical or food preparation of claim 14, comprising a product selected from the group consisting of skin care products, hair care products, body care products and sunscreen products.

* * * * *